(12) United States Patent
Keillor et al.

(10) Patent No.: US 7,700,375 B2
(45) Date of Patent: Apr. 20, 2010

(54) FLUORESCENT LABELING OF SPECIFIC PROTEIN TARGETS IN VITRO AND IN VIVO

(75) Inventors: Jeffrey W. Keillor, Montréal (CA); Stephen W. Michnick, Montreal (CA); Stéphane Girouard, Longueuil (CA)

(73) Assignee: Valorisation-Recherche, LP, Montreal, Quebec (CA)

( * ) Notice: Subject to any disclaimer, the term of this patent is extended or adjusted under 35 U.S.C. 154(b) by 0 days.

(21) Appl. No.: 11/153,398

(22) Filed: Jun. 16, 2005

(65) Prior Publication Data
US 2006/0147948 A1    Jul. 6, 2006

Related U.S. Application Data

(60) Provisional application No. 60/579,686, filed on Jun. 16, 2004.

(51) Int. Cl.
*G01N 33/533*    (2006.01)
*G01N 33/53*    (2006.01)

(52) U.S. Cl. .................. 436/546; 435/7.1; 435/7.92
(58) Field of Classification Search .............. 436/544, 436/546, 172; 435/7.1, 6
See application file for complete search history.

*Primary Examiner*—Shafiqul Haq
(74) *Attorney, Agent, or Firm*—Isaas A. Angres

(57) ABSTRACT

New methods are provided for the post-genomic era that will permit the analysis of the dynamic expression and localization of gene products in living cells. Herein we propose the development of such a method from a bioorganic approach involving organic synthesis and protein engineering. Specifically, novel compounds bearing two maleimide groups attached directly to fluorescent cores will be prepared, whose latent fluorescence is quenched until their maleimide groups undergo a specific thiol addition reaction. Complementary a-helical proteins are designed bearing two cysteine residues appropriately positioned to react with our novel fluorogens. Genetically fusing our helical probe peptides to test proteins of interest, we can selectively label the target sequence in living cells with our small synthetic fluorogenic molecules. The scope of this technique is described in the context of studying protein localization and protein-protein interactions in living cells.

5 Claims, 12 Drawing Sheets

FLUORESCENT LABELING OF SPECIFIC PROTEIN TARGETS IN VITRO AND IN VIVO

This application claims the priority benefit under 35 U.S.C. section 119 of U.S. Provisional Patent Application No. 60/579,686 entitled "Fluorescent Labeling Of Specific Protein Targets In Vitro And In Vivo", filed Jun. 16, 2004, which is in its entirety herein incorporated by reference.

FIELD OF THE INVENTION

The present invention relates to determining the function of novel gene products. The invention further relates to compositions and methods for the synthesis of selective labels for proteins via a peptide fragment which is either helical or is induced to become helical by the labeling molecule. The resultant labeled protein can be detected in vitro or in a living cell and its dynamic turnover, localization and interactions with other molecules can be detected.

BACKGROUND OF THE INVENTION

The sequencing of the human genome has allowed the identification of a huge number of putative genes.[1,2,3] However, the function of only a small number of these can be inferred from their primary sequences. New techniques are needed to cope with the task of assigning functional roles to these gene products. This implies determination of how, when and where they are involved in specific biochemical pathways. Ideally, these methods will allow the rapid screening of substantial subsets of the sum of a genome's products. Although many proteins have been identified by functional cloning of novel genes, this 'expression cloning' approach remains a significant experimental challenge. Certain proteomic methods have been designed for broad and rapid screening, but they are largely limited to in vitro application and do not necessarily provide information pertinent to living cells. Moreover, although these methods can verify what genes are expressed, it is even more important to understand the dynamic patterns of in vivo protein expression and localization. For this, more powerful methods of detection of specific proteins and their interactions inside living cells are urgently required.

Several labeling techniques have been developed that involve the use of fluorescent dyes bearing reactive functional groups such as succinimidyl esters or maleimides, known to react with amines or thiols.[4,5,6] Although these techniques are typically non-specific—many such functional groups exposed on the surface of any protein may be labeled—the characterization of these small molecule fluorophores teaches us the general requirements for solubility and cell permeability. However, in the proteomic context, they do not provide a general means for gathering information on specific protein targets.

The genetic fusion of target proteins to fluorescent proteins such as jellyfish green fluorescent protein (GFP) is another technique that has seen broad application.[7] However, there are some serious limitations of this method. For example, the entire sequence of GFP must be properly folded into its 11-stranded β-barrel structure for it to function as a fluorophore, but it folds very slowly and is prone to aggregation. Moreover, GFP fluorescence suffers from low quantum yields, is sensitive to the environment of its fusion with test proteins and is also difficult to distinguish from the autofluorescent background of living cells. Furthermore, the steric bulk of a 27 kDa β-barrel protein can significantly perturb the interactions of the test proteins.[7,8] In summary, the use of GFP derivatives can be inefficient and intrusive.

Of greater pertinence to this proposal is Tsien's use of certain small organometallic molecules that have been shown to react specifically with four cysteine residues.[9,10,11] These cysteine residues were arranged in what was originally thought to be an α-helical conformation, but it was later shown that a β-turn conformation was optimal for their reaction with the fluorogenic arsenate compounds employed. In the application of this method, the fusion of a small probe protein of appropriate sequence to the target test protein allows it to be fluorescently labeled in live cells. Although these metallic complexes may not be broadly applicable to in vivo protein labeling studies due to their acute toxicity, they demonstrate nevertheless the feasibility of the use of small molecules to react preferentially with multiple thiol groups on a protein scaffold even in live cells, in the presence of several equivalents of simple native thiols. Furthermore, these small molecules illustrate the possibility the specific labeling of a test protein expressed as a fusion protein with a target sequence comprising an appropriate protein conformational motif. In this way, the seminal work of Tsien demonstrates the validity of our approach and the feasibility for our fluorometric assay proposed herein.

Over the last several years,[13,14] we have conceived a rational design strategy parallel to Tsien's approach in which de novo, minimal peptides of less than 30 amino acids will react with novel synthetic probe reagents that fluoresce only after their reaction with the minimal folded peptide.

SUMMARY OF THE INVENTION

The present invention seeks to provide the above-mentioned needs for which the prior art is silent. The present invention provides a general strategy to detect the dynamics of protein localization and turnover as well as protein-protein, protein nucleic acid and protein-carbohydrate interactions. The present invention also provides for a general strategy to screen small molecule, small interfering RNAs or to study he effects of any other molecular entity on protein dynamics or protein interactions with other molecules. In a preferred embodiment, the instant invention seeks to provide a spontaneous labeling of peptides with fluorophores that requires no other molecules to detect their fluorescence and which are not toxic to living cells. In one such embodiment, maleimide groups have long been used in applications that exploit their propensity to react selectively with thiol groups, undergoing addition reactions through their C2=C3 double bond.[15] Maleimides are also known to quench fluorescence, probably due to their introduction of a lone pair whose lowest energy n→π* transition is forbidden and leads to a long lived excited state that relaxes through non-radiative processes. The thiol addition reaction breaks the conjugation of the maleimide group, altering the energy levels of its molecular orbitals and removing its capacity to quench fluorescence.[16] These properties were demonstrated recently in the characterization of a naphthopyranone derivative bearing a maleimide group whose fluorescence increased dramatically upon reaction with glutathione.[17,18] We reasoned that if a fluorogen was prepared bearing two maleimide groups, then its latent fluorescence would only be realized upon its reaction with two equivalents of thiol. Furthermore, if the positioning of maleimide groups was such that they were separated by a precise distance, then the resulting fluorogen should react rapidly and specifically with compounds presenting two sulfhydryl groups separated by the corresponding distance. We have synthesized a small series of such dimaleimide fluorogens and characterized their reactions with thiols and dithiols, as well as the changes in their fluorescent properties accompanying these reactions, confirming the potential of their application to for the specific labeling of protein targets.[13,14,19]

Probe protein targets were designed to react efficiently with their complementary dimaleimide groups, through two cysteine residues whose pendant thiol groups would be solvent exposed, sterically unhindered and separated by an appropriate distance, namely that between the corresponding maleimide groups, as determined by molecular modeling. We chose to work with small (~30 amino acid) α-helical proteins since this secondary structural motif is of sufficiently limited conformational flexibility so as to allow the precise positioning of cysteine residues. Furthermore, the mass of these probe proteins is around one-tenth of the mass added in previous GFP-based assays, representing much less perturbation of native protein localization and function and allowing greater sensitivity for detection of biologically relevant events. With two cysteine residues positioned at a fixed geometry, spatially separated by a defined distance, these probe proteins will be able to react with our dimaleimide fluorogenic compounds, forming a fluorescent covalent adduct.

In preliminary experiments designed to provide proof of principle,[20] we prepared a dicysteine mutant of a fragment of Fos,[21] an α-helical[22] protein whose recombinant expression has been published previously.[23] The results from initial in vitro experiments demonstrate the efficiency of the reaction of our dimaleimide fluorogens with the dicysteine α-helical protein as well as the markedly superior fluorescence of the stoichiometric protein-fluorogen adduct formed on reaction of both maleimide groups.[20] Recent in vivo experiments have confirmed the specificity of this reaction, even in the cytosolic milieu inside living mammalian cells,[20] validating the design of our technique (see Previous Results, below).

This novel fluorogenic labeling method has several features that make it potentially appropriate for genomic screening of molecular interactions: 1) This approach is not limited to a single assay, but represents a series of assays, of which the fluorogen and protein target sequence may be chosen according to their efficacy in a particular cell type appropriate to the study of the interactions of a given class of proteins. 2) The proposed method can be automated and tailored for high-throughput fluorescent screening. 3) The fluorogens are designed at the level of the atomic structure and three-dimensional conformation of the target protein motifs, allowing control over the flexibility and specificity of the probe fragments used.

Furthermore, this fluorogenic labeling method has the potential to improve upon existing strategies: 1) The relatively small probe proteins that we will use have a far smaller potential to disrupt the localization and interactions of the native protein than the relatively large protein fragments used in other methods. 2) Since the signal reaction is a simple reaction between proteins thiols and a thiol-selective small molecule fluorogen, it is less sensitive to the effects of variation of cellular conditions than the folding of fluorescent protein applications. 3) The inherent flexibility of this method to design fluorogenic probes with many different spectral qualities that react specifically with different protein targets will allow the encoding of protein interactions in different ways. This includes the potential multiplexed analysis of protein expression and turnover in vivo and in vitro.

In a preferred embodiment of the invention we describe the development and refinement of the minimal, covalent protein-labeling fluorescent assay. This development must take place in two complementary objectives: development of the fluorogen, and of appropriate protein probes. In a second embodiment of the invention we demonstrate the application of this method to label target fusion proteins in vitro and in vivo. A third embodiment of the invention comprises the specific labeling of two different target proteins with two different fluorogens, permitting the detection of their interaction through FRET-based fluorescent assay.

The present invention also provides a spatially-specific labeling assay for the detection of presence, location and temporal dynamics of target molecules and their interactions comprising contacting said target molecules with a molecule under conditions wherein said molecule specifically reacts with said target molecule, said target molecule comprising two or more nucleophilic moieties capable of specifically reacting with said molecule, wherein reaction between the molecule and nucleophiles of the target molecule is independent of any other molecular process and wherein said reaction results in a detectable signal.

The instant invention is also directed to an assay method for detecting molecules comprising: generating: 1) at least a first dimaleimide molecule and 2) at least a first target molecule linked to a protein, or 3) nucleic acid molecules that code for 2) and subsequently allowing said nucleic acid molecules to produce their coded products; then, (A) allowing reaction of said target molecule with said dimaleimide molecule; and (B) detecting a signal from said complex of target molecule and dimaleimide molecule.

The invention further provides an assay method for detecting biomolecular interactions, said method comprising: generating: 1) at least a first dimaleimide molecule and 2) at least a first target molecule linked to an interacting protein, or 3) nucleic acid molecules that code for 2) and subsequently allowing said nucleic acid molecules to produce their coded products and then, (A) allowing reaction of said target molecule with said dimaleimide molecule; and then generating 4) at least a second dimaleimide molecule and 5) at least a second target molecule linked to a second interacting protein, or 6) nucleic acid molecules that code for 5) and subsequently allowing said nucleic acid molecules to produce their coded products; then, (C) association of said first and second dimaleimide molecules through interaction of said first and second target molecules linked to said first and second interacting proteins; and (D) detecting a signal from said complex of target molecules and dimaleimide molecules.

The invention is further directed to a composition comprising a dimaleimide molecule, said dimaleimide molecule having the following formula:

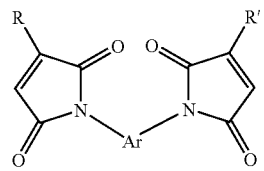

wherein: each R or R', independently, is $R_a$ or $OR_a$ and $R_a$ is H, $C_1$-$C_4$ alkyl, $CH_2CO_2H$, $CH_2CH_2OH$ or CN and Ar is a rigid aromatic skeleton comprising one to four fused aromatic rings such as phenyl, naphthyl, anthracene, fluorene, pyridine, pyrimidine, purine, indole. wherein the substituent maleimide groups are positioned around the aromatic core in such manner that they are separated by 5, 10 or 15 Å, conferring complementarity for reaction with the target target molecule and including fluorescent aromatic derivatives such as fluorescein, rhodamine, eosin, thionine, safranin or coumarin; or said dimaleimide molecule has the following formula:

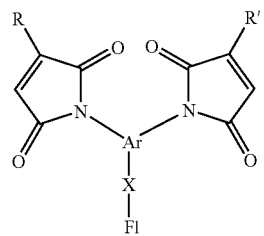

wherein: each R or R', independently, is $R_a$ or $OR_a$ and $R_a$ is H, $C_1$-$C_4$ alkyl, $CH_2CO_2H$, $CH_2CH_2OH$ or CN and Ar is a rigid aromatic skeleton comprising one to four fused aromatic rings such as phenyl, naphthyl, anthracene, fluorene, pyridine, pyrimidine, purine, indole, etc. X is a spacer sequence that includes $C_1$-$C_4$ alkyl, $OCH_2CH_2O$, $NHCO(C_1$-$C_4H_2$ alkyl)NHCO, $CONH(C_1$-$C_4CH_2$ alkyl)NHCO, $NHCO(C_1$-$C_4CH_2$ alkyl)CONH, $CONH(C_1$-$C_4CH_2$ alkyl)CONH, and F1 is a fluorophore such as fluorescein, rhodamine, eosin, thionine, safranin, and coumarin.

DESCRIPTION OF THE PREFERRED EMBODIMENTS

Figure 1:
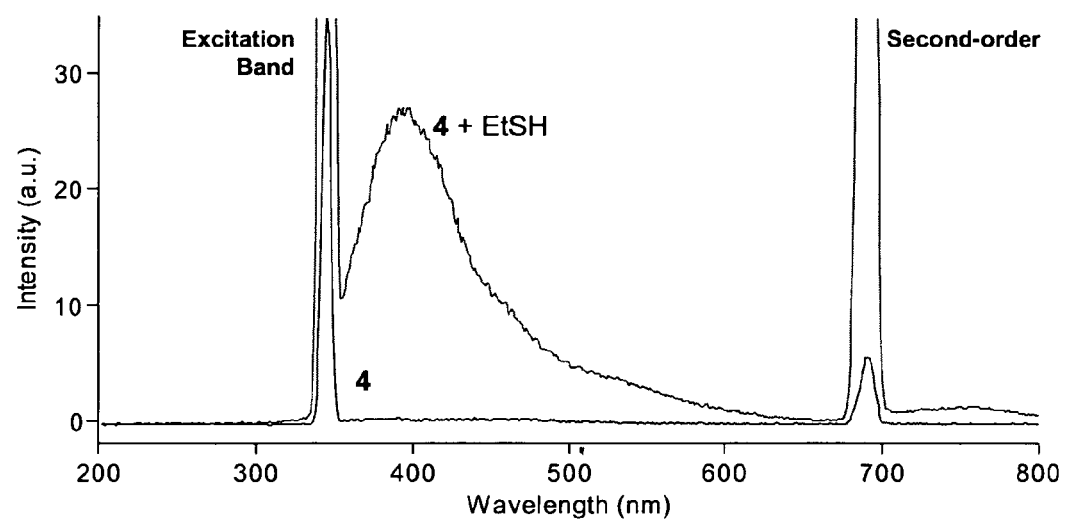
FIG. 1: Marked increase in fluorescence upon addition reaction of ethanethiol with two maleimide groups of fluorogen 4.

Our previous results provide ample proof of principle for our first two specific objectives, namely: 1) the development of the covalent protein-labeling fluorescent assay and 2) the application of this method to the labeling of target proteins in vitro and in vivo.

1) Assay Development

Fluorogen Design

Maleimide groups are known for undergoing specific thiol addition reactions. They have been used in the context of analytical chemistry for the detection of thiols, based on the specificity of their reaction,[24] and have been applied with success to protein labeling in vivo.[4] Their ability to quench fluorescence is also well-known[16] and our initial experiments were designed to test our hypothesis that a latent fluorophore bearing two maleimide groups would have to react at both maleimide groups in order to fluoresce, since one unreacted maleimide group would be sufficient to quench fluorescence.

Fluorogen Synthesis

Shown in Schemes 1 and 2 are the routes taken to prepare fluorogenic coumarin derivatives 4 and 13, by the reaction of their corresponding diamino derivatives with maleic anhydride.[25], Diamino derivative 3 are prepared according to a previously published synthetic route,[26] which also formed the basis of the route used to prepare the novel diamine 12. For most of the steps, the synthesis can be understood by artisans acquainted with the art; however, the key step involving the synthesis of the maleimide ring is problematic. As has been reported, the weak nucleophilicity of the aromatic amines and the limited solubility of the synthetic precursors lowers the yield of this transformation that introduces two maleimide groups, each requiring two reaction steps.[27]

Scheme 1

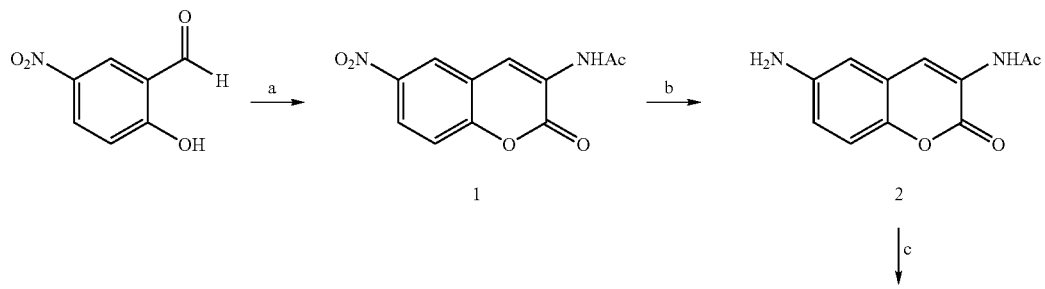

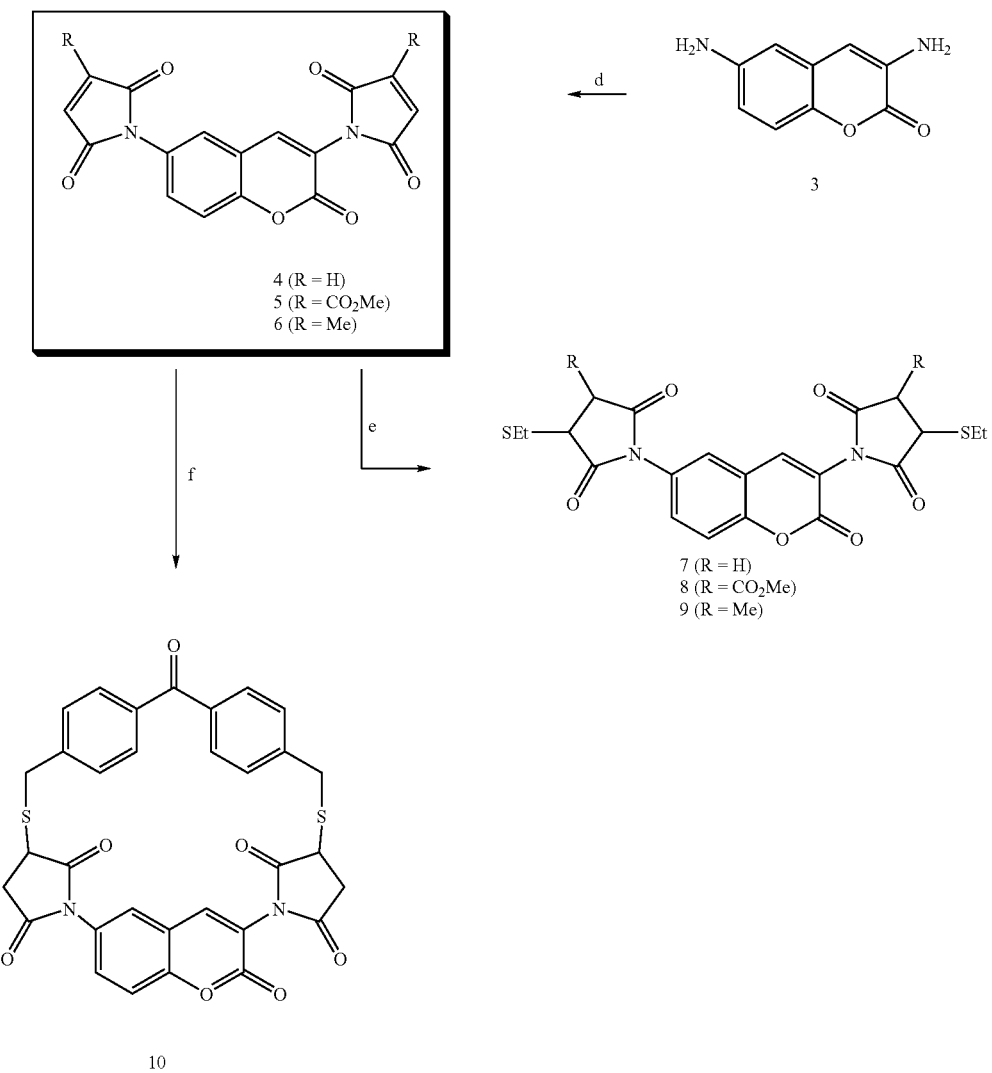
- (a) N-acetylglycine, NaH, Ac₂O, rt, 61%;
- (b) Pd/C (10% H₂O), NaBH₄, MeOH, 57%;
- (c) EtOH, HCl, reflux, 65%;
- (d) (i) maleic anhydride, CHCl₃, reflux,
  (ii) Ac₂O, AcONa, 100° C., 20% (2 steps);
- (e) EtSH, CHCl₃ or DMSO, rt, 83-85%;
- (f) BMMB, NEt₃, CHCl₃, reflux, 78%.
Scheme 2
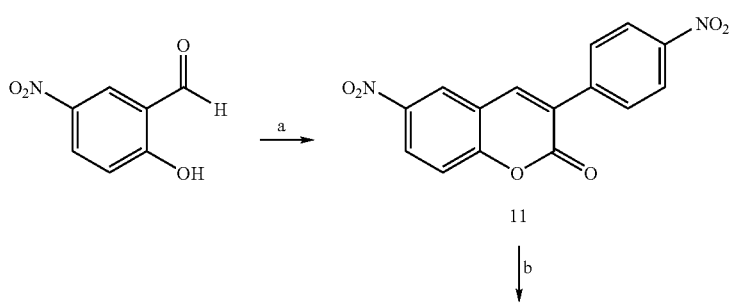

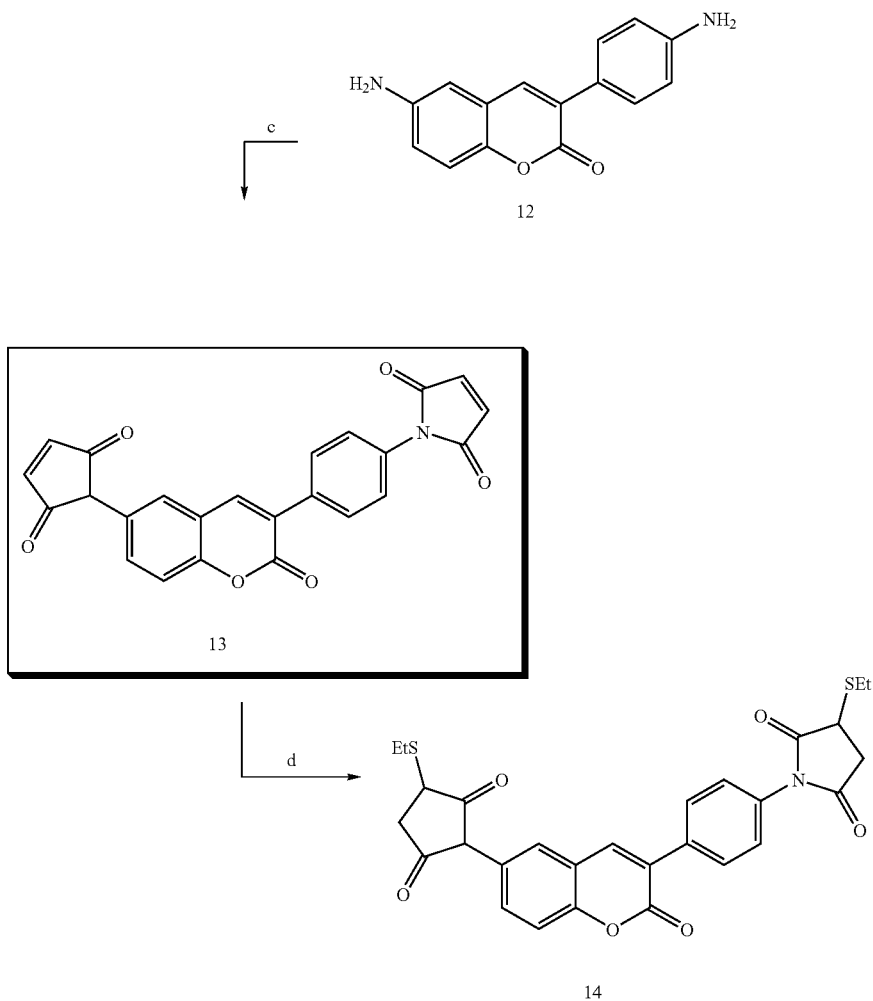

(a) 4-nitrophenylacetic acid, Ac$_2$O, NaH, rt, 70%;
(b) Pd/C (10% H$_2$O), NaBH$_4$, MeOH, 63%;
(c) (i) maleic anhydride, CHCl$_3$, reflux,
    (ii) Ac$_2$O, AcONa, 100° C., 20% (2 steps)
(d) EtSH, DMSO, rt, 89%.

In Schemes 3 and 4 are shown the syntheses of fluorogens 15 and 20, bimaleimide derivatives of naphthalene. The synthesis of 15 requires only the facile addition of the maleimide group to the commercially available diaminonaphthalene, whereas the synthesis of 20 is more circuitous.[28] Nitration of commercially available 1,8-naphthalic anhydride yielded 3,6-dinitro derivative 17 and a small amount of the 3,5- and 4,5-dinitro derivatives, whose formation is limited to <20% at reaction temperatures between 10° C. and 20° C.[28] These derivatives are easily separable by chromatography, giving compound 17 in good yield. From this anhydride the imide of L-aspartic acid dimethyl ester (18) is formed in moderate yield over the two steps. Palladium-catalyzed reduction yields the corresponding diamine 19 in modest (unoptimized) yield, with complete consumption of starting material, suggestive of the formation of side-products or degradation. The subsequent reaction with maleic anhydride[25] gives the desired fluorogen 20 in 19% over these two steps.

Although the yields of the individual steps of these four synthetic schemes have not been optimized, we have been able to scale up these reactions to provide enough of each fluorogen for the subsequent characterization of their reactivity and fluorescence.

Scheme 3
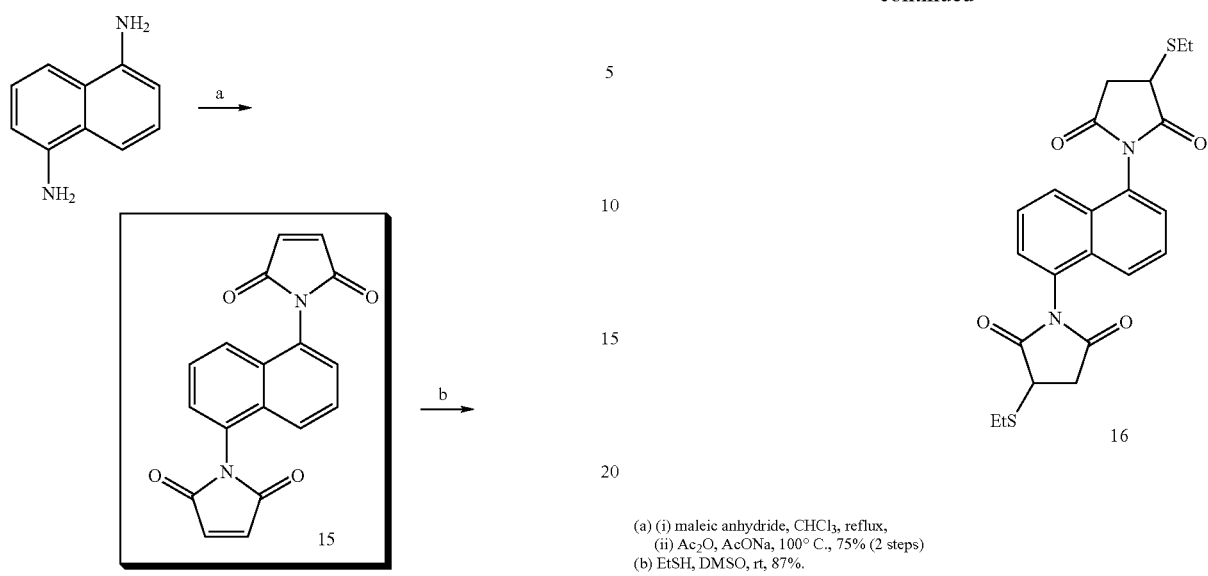
(a) (i) maleic anhydride, CHCl₃, reflux,
(ii) Ac₂O, AcONa, 100° C., 75% (2 steps)
(b) EtSH, DMSO, rt, 87%.
Scheme 4
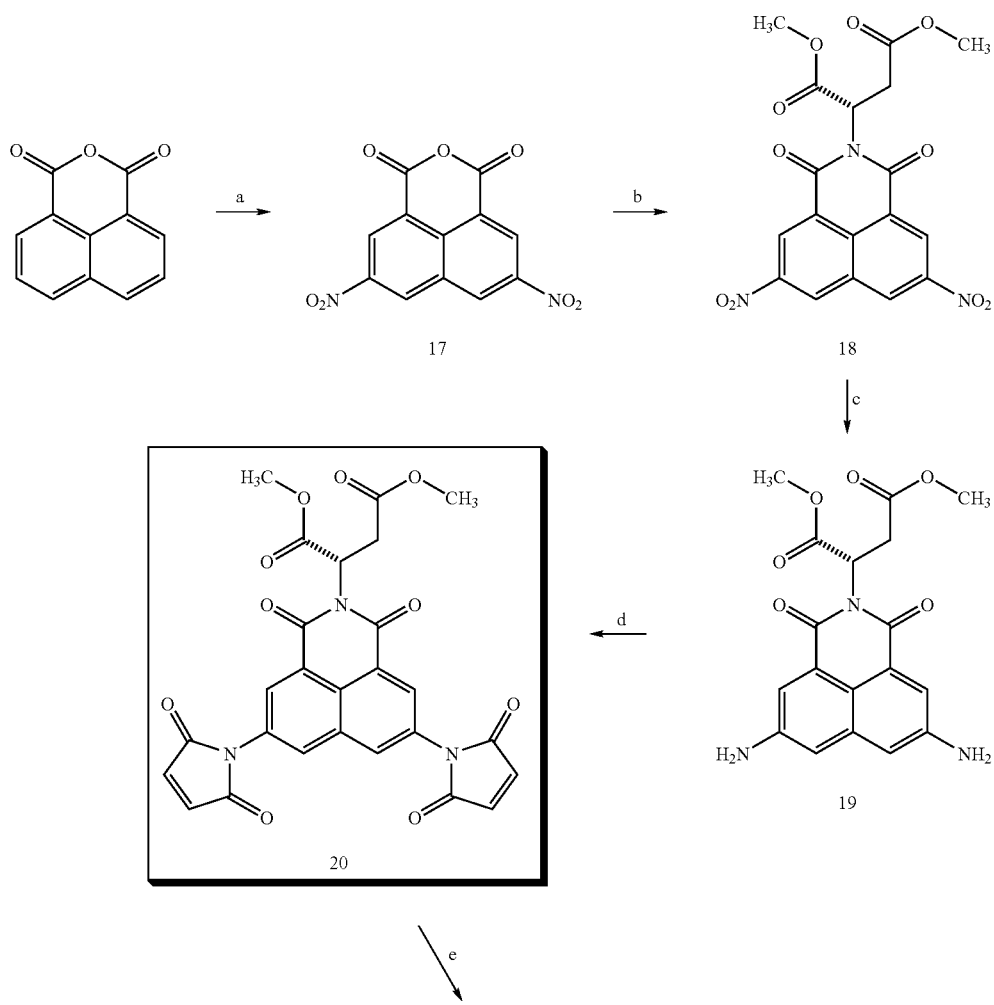

-continued

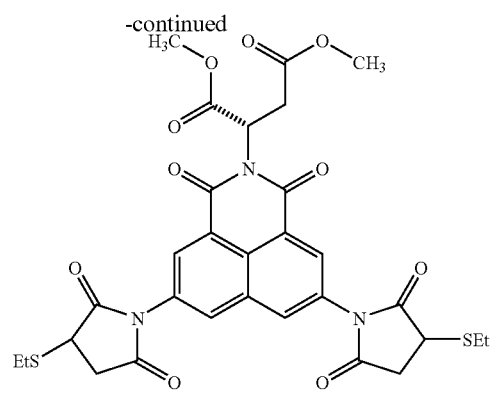

21

(a) H$_2$SO$_4$, HNO$_3$, 10-20° C., 72%
(b) CH$_3$CN, TEA, L-aspartic acid dimethyl ester•HCl, 90° C., 45%
(c) H$_2$/Pd/C, 150 psi, THF, 49%
(d) (i) maleic anhydride, CHCl$_3$, reflux,
    (ii) Ac$_2$O, AcONa, 100° C., 19% (2 steps).
(e) EtSH, DMSO, rt, 89%.

Thiol Addition Reaction

The addition of 3 mM ethanethiol to 1 mM solutions of 4 or 13 prepared in 9:1H$_2$O:DMSO leads to a marked increase in fluorescence over 3 hours. The fluorescence spectra obtained upon excitation at 350 nm before and after the reaction of ethanethiol with compound 4 are shown in FIG. 1.

Figure 2:
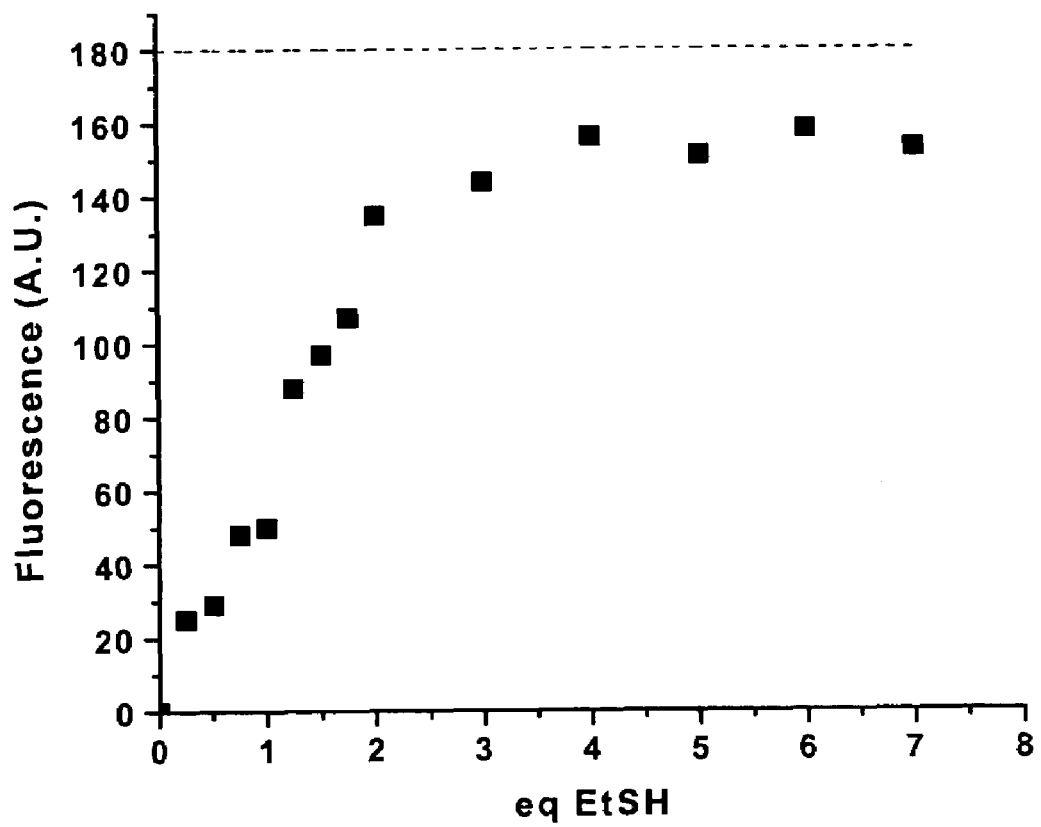
FIG. 2: Increase in fluorescence upon addition of up to two equivalents of ethanethiol to fluorogen 4. Dotted line shows fluorescence of same concentration of authentic thiol adduct product 7, synthesized and purified independently (see Scheme 1).
Figure 3:
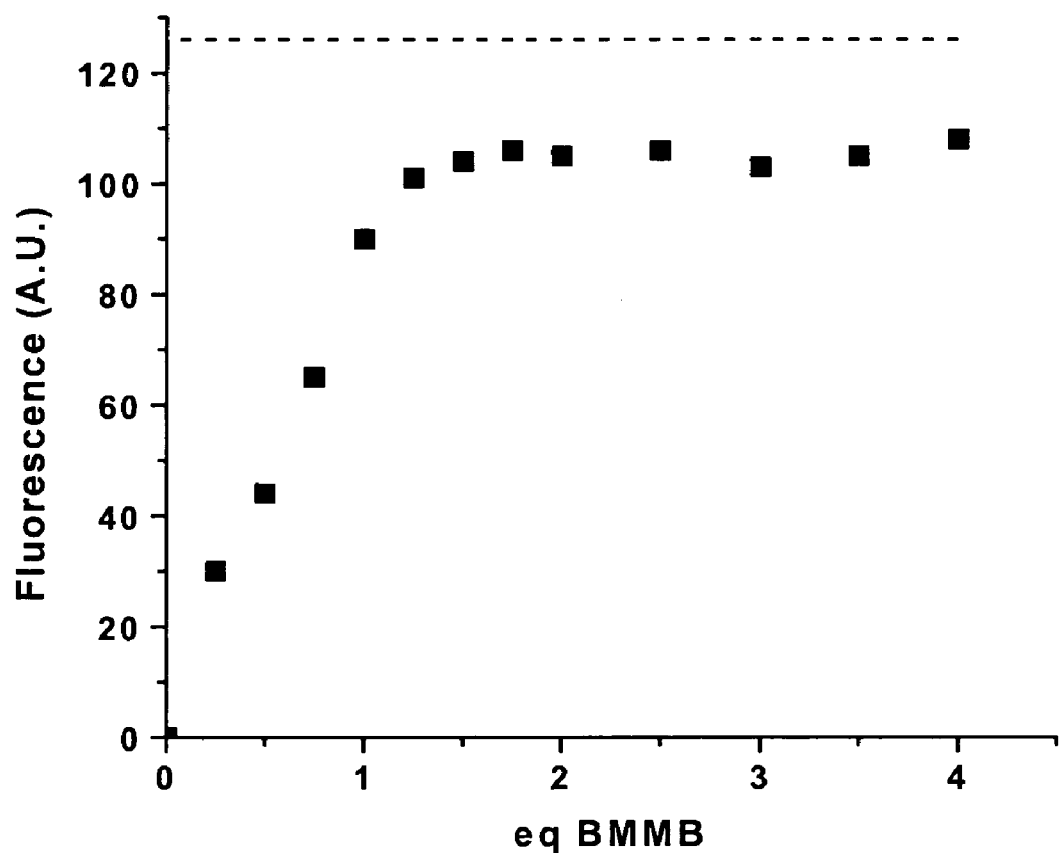
FIG. 3: Increase in fluorescence upon addition of up to one equivalent of dithiol BMMB to fluorogen 4. Dotted line shows fluorescence of same concentration of authentic dithiol adduct product 10, synthesized and purified independently (see Scheme 1).

For both compounds 4 and 13, the increase in fluorescence intensity was found to be directly proportional to the number of equivalents of thiol added, increasing with added thiol until a plateau was reached at ~2.2 equivalents of thiol, consistent with the formation of fluorescent dithiolated adduct (i.e. formation of 7 (Scheme 1), shown in FIG. 2 for fluorogen 4). Based on this observation, we reasoned that compounds 4 and 13 should also react efficiently with one equivalent of a dithiol bearing two sulfhydryl groups separated by an appropriate distance. As can be seen in FIG. 3, the reaction of 4 (1 mM in DMSO) with 4,4'-bis(mercaptomethyl)benzophenone (BMMB, synthesized according to established literature procedures)[29,30] leads to an increase in fluorescence proportional to the number of equivalents of dithiol added until a plateau is reached at one equivalent of dithiol. That this plateau was reached at ~1.0 equivalent of dithiol demonstrates the superior ability of an appropriately designed dithiol (BMMB) to react with both maleimide groups of an appropriately designed fluorogen (4), to form a single dithiol adduct (10), as opposed to undergoing two separate intermolecular reactions. That is, after fluorogen 4 undergoes an initial addition reaction with BMMB, the second addition reaction with the pendant sulfhydryl group of BMMB is intramolecular and presumably much faster (Scheme 5).

Scheme 5

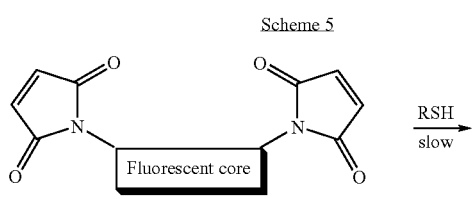

-continued

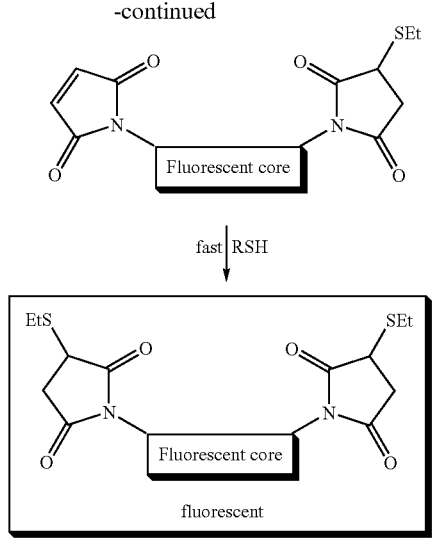

In the case of simple thiols, the second thiol addition reaction would also be intermolecular, and not subject to relative acceleration from any entropic advantage, so it remained to be seen if the first or second addition reaction were rate-limiting. If the first intermolecular addition reaction is indeed significantly slower than the addition of a second equivalent of simple thiol to the monothiolated adduct, then the rate law for the formation of fluorescent addition product should be first order in thiol concentration, based on a rate-limiting first addition reaction (equation 1).

$$\frac{d[P]}{dt} = k_1[RSH][4] \qquad (1)$$

Conversely, if the second step of Scheme 5 were slow, the rate law would be second order in simple thiol, reflecting the presence of two equivalents of thiol in the activated complex at the transition state of the rate-limiting step (equation 2).

$$\frac{d[P]}{dt} = k_2[RSH][4][RSH] = k_2[RSH]^2[4] \quad (2)$$

Figure 4:
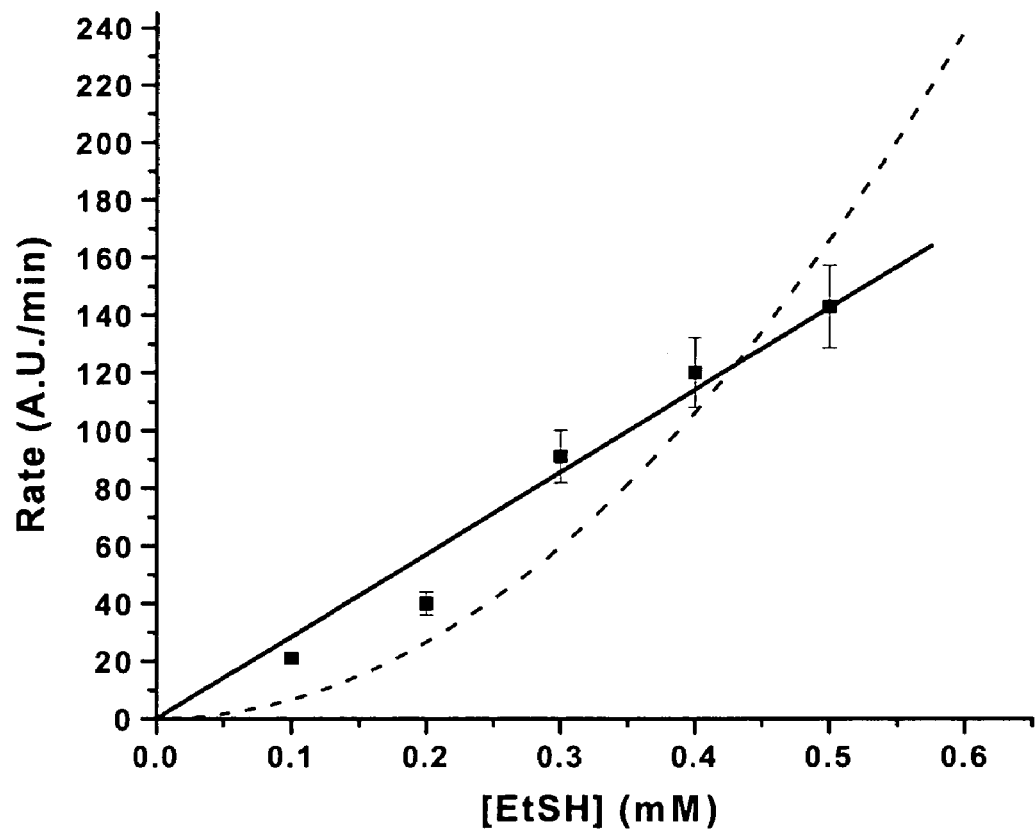
FIG. 4: Linear dependence of rate of thiol addition reaction of 4 on concentration of added ethanethiol (solid line). Shown as a dotted line is the poor fit of the rate data to a rate law second order in thiol.

In fact, when the concentration of added thiol was varied, the rate of the fluorogenic reaction was found to increase linearly, and not exponentially, as shown in FIG. 4. This shows that even for simple thiols, the second addition reaction is faster than the first; apparently, the initially formed monothiolated adduct is activated toward the second thiol addition reaction. In the case of dithiol addition, this second addition reaction with a sulfhydryl group would be intramolecular, and presumably even faster.

Product studies carried out for the reaction of 4 with simple thiols support the hypothesis that the second addition reaction is faster than the first. Initial experiments involved the addition of ethanethiol to 4 and attempts to separate and characterize the dithiolated and monothiolated adducts. However, no significant peak corresponding to the putative monothiolated adduct could be isolated by flash chromatography, so an experiment was designed to facilitate the separation of the monothiolated and dithiolated adducts by capillary electrophoresis (CE, see Experimental Section). By using 3-mercaptopropionic acid as a simple thiol, we ensured that at basic pH, any monothiolated adduct would singly negatively charged, due to ionization of the carboxylate group, whereas the dithiolated product would be doubly negatively charged. The results of this analysis showed that during the reaction of 4 with up to 2 equivalents of 3-mercaptopropionic acid, a trace quantity of monothiolated adduct was formed for reaction with <1.5 equivalents of thiol. (For the reaction with 13, no monothiolated product was detectable.[13]) Furthermore, the previously recorded fluorescence of the reaction mixture of 4 and 3-mercaptopropionic acid correlates linearly with the relative proportion of dithiolated adduct (data not shown).[13] Taken together, these experiments indicate that during the reaction of dimaleimido fluorogens with small thiols, very little monothiolated adduct is formed, and formation of dithiolated adduct predominates. Furthermore, the dithiolated adduct appears to be the sole contributor to the observed fluorescence; additional studies with bulkier protein thiols will be shown to corroborate the hypothesis that the monothiolated adduct does not fluoresce (vide infra).[19]

Figure 5:
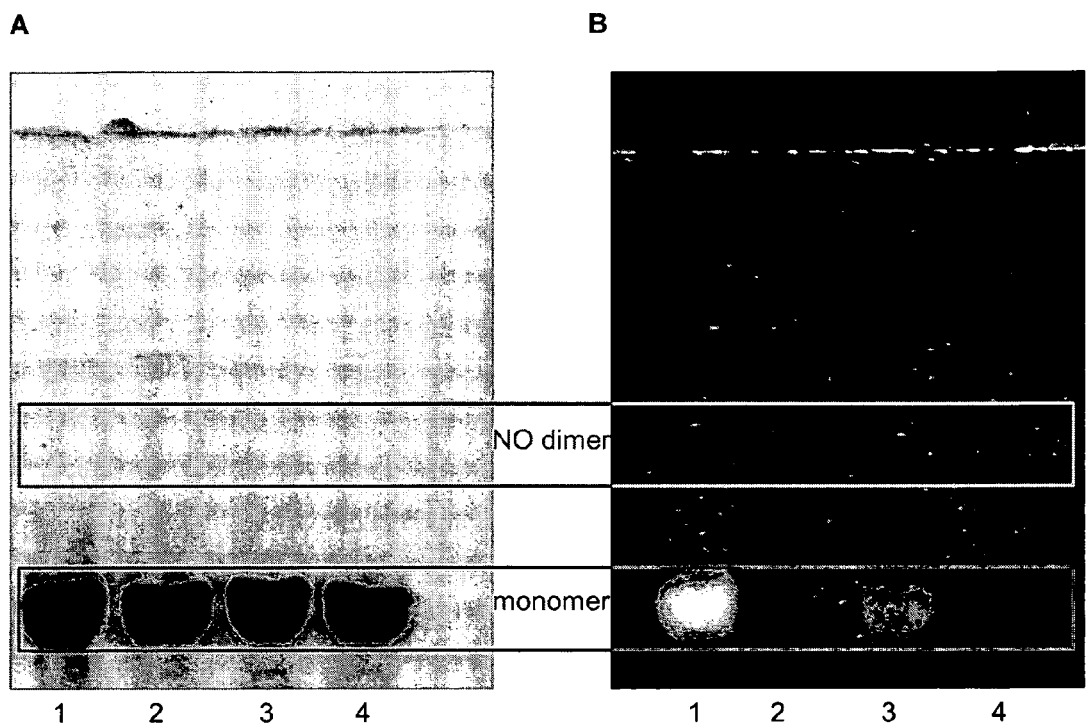
FIG. 5: SDS-PAGE analysis of the reaction of fluorogens 13 and 20 with α-helical proteins containing one (mCys-Fos) or two (diCys-Fos) cysteine residues: Protein concentration 0.242 mM. Lane 1: diCys-Fos+20 (0.5 mM); lane 2: mCys-Fos+20 (0.5 mM); lane 3: diCys-Fos+13 (0.05 mM); lane 4: mCys-Fos+13 (0.05 mM). A) Coomassie blue staining; B) fluorescence (UV excitation)

Reactions involving nucleophilic addition of thiols typically proceed through nucleophilic attack by their thiolate anions, without the requirement for general base assistance. As such, reaction rates are observed to increase with pH until a plateau is reached above the $pK_a$ of the nucleophilic thiol. The reaction of 13 with ethane thiol was studied for its pH dependence[14] from pH 5.5-8.5, under pseudo-first order conditions (2.0 mM EtSH and 0.1 mM 13) in buffered aqueous solutions with DMF added to a final concentration of 10% for solubility. Over this pH range, the thiol addition reaction was mono-exponential and the background reaction negligible, allowing the facile measurement of the pseudo-first-order rate constants for the addition reaction as a function of pH (FIG. 5). However, an apparent consecutive degradation reaction, resulting in a loss of fluorescence, became increasingly important at higher pH and prevented the measurement of first-order rate constants above pH 8.5. Due to this limitation, the kinetic $pK_a$ expected to correspond to the $pK_a$ of ethane thiol (10.6) could not be observed, but the pH dependence shown in FIG. 5 is consistent with the attack of ethane thiol in its basic form.

First-order rate constants for the reaction of 0.1 mM 13 with 2.0 mM ethanethiol in DMF were also measured as a function of temperature from 10-40° C. Over this temperature range, the observed rate constants increased slightly with temperature, but varied by less than a factor of 2, and evaporation of ethanethiol was problematic at 40° C. For these reasons, precise quantitative analysis of the effect of temperature (for example, in the form of an Eyring plot) was not possible. However, the results demonstrate that at room temperature or 37° C., the highest temperature envisioned for the practical application of this method, the reaction is more rapid than at lower temperatures. This indicates that in the ultimate application of this method to protein labeling, the addition reaction should be carried out at room temperature rather than on ice.

In an alternate synthesis strategy, we will prepare a series of aromatic compounds bearing two maleimide groups using typical nitration, reduction, protection/deprotection and maleidimide formation methodology (Schemes 6-8). These maleimide groups will thus be held in rigid conformations separated by fixed distances designed to be complementary to those between the cysteine resiudes of our target peptide sequences. These dimaleimide fragments will also bear alkyl amines that will be used to attach a given dimaleimide fragment to any member of a series of fluorophores that will be prepared or obtained commercially, bearing a free carboxylate group (e.g. carboxylic acid derivatives of fluorescein, rhodamine, coumarin, etc). This ligation will take place via the formation of a robust amide bond, using a rich variety of well-known peptide coupling methods. In this way, an expanded library of next generation dimaleimide fluorogens will be prepared, comprising fluorogens with different target protein specificities and different fluorescent spectral properties.

Scheme 6: Synthesis of ~5-Å dimaleimide fragments (dM-5)

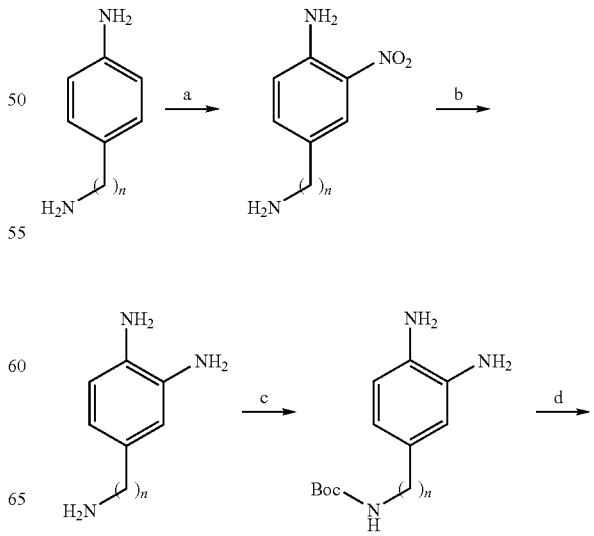

-continued

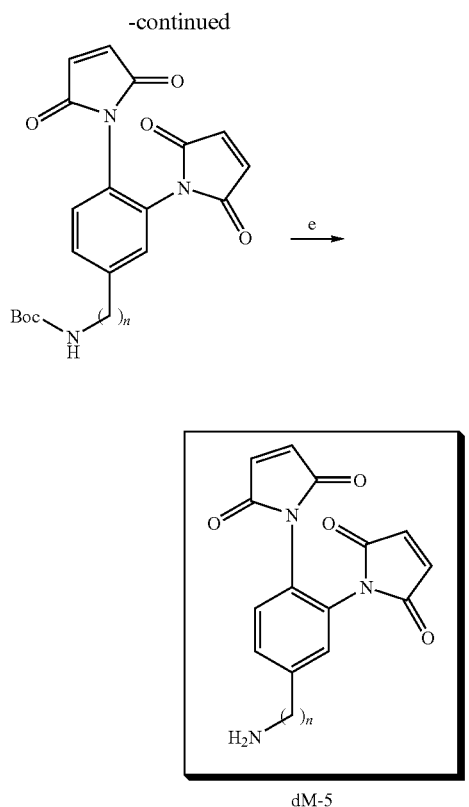

dM-5

(a) H₂SO₄, HNO₃, 10-20° C.
(b) H₂/Pd/C, 150 psi, THF
(c) (Boc)₂O, Et₃N, MeOH at 0° C.
(d) (i) maleic anhydride, CHCl₃, reflux,
    (ii) Ac₂O, AcONa, 100° C.
(e) TFA, anisole, CH₂Cl₂ at 0° C.

Scheme 7: Sythesis of ~10-Å dimaleimide fragments (dM-10)

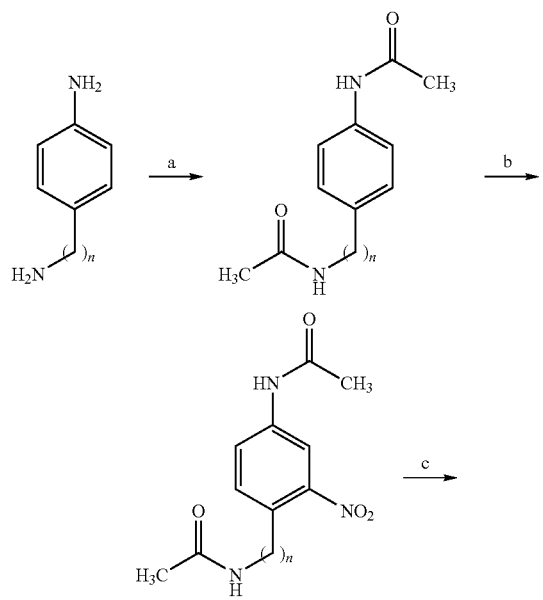

-continued

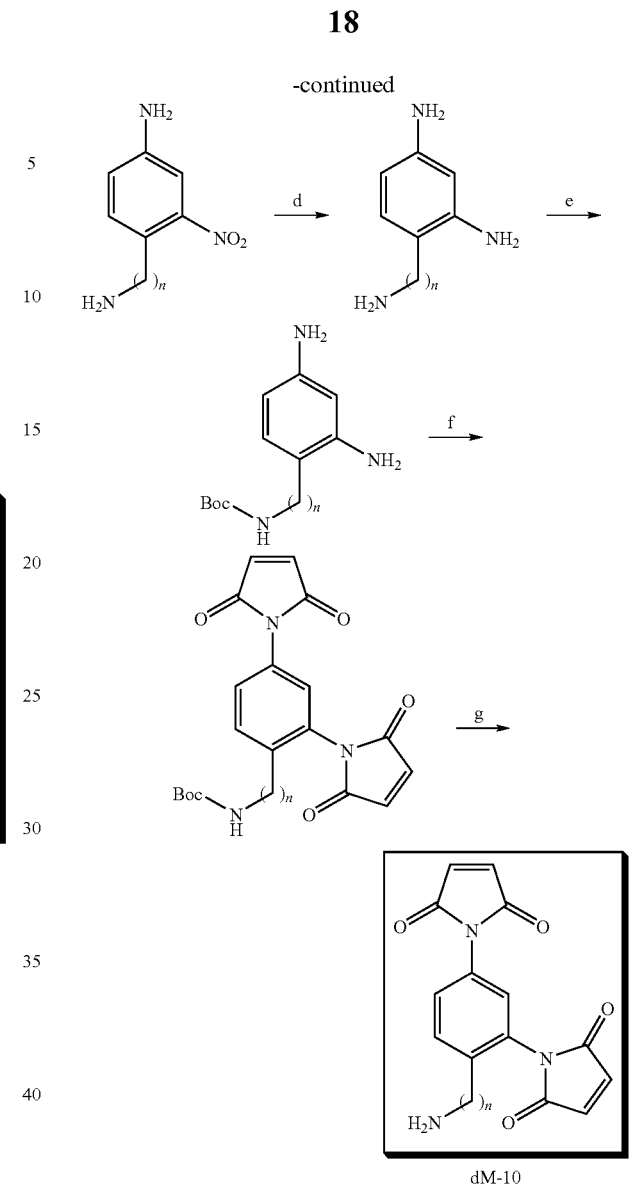

dM-10

(a) Ac₂O, NEt₃, MeOH at 0° C.
(b) H₂SO₄, HNO₃, 10-20° C.
(c) NaOH, THF/H₂O
(d) H₂/Pd/C, 150 psi, THF
(e) (Boc)₂O, Et₃N, MeOH at 0° C.
(f) (i) maleic anhydride, CHCl₃, reflux,
    (ii) Ac₂O, AcONa, 100° C.
(g) TFA, anisole, CH₂Cl₂ at 0° C.

Scheme 8: Synthesis of ~15-Å dimaleimide fragments (dM-15)

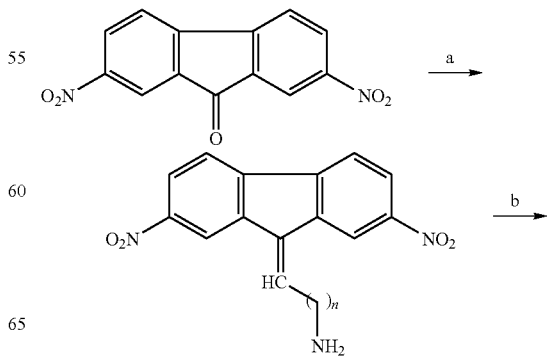

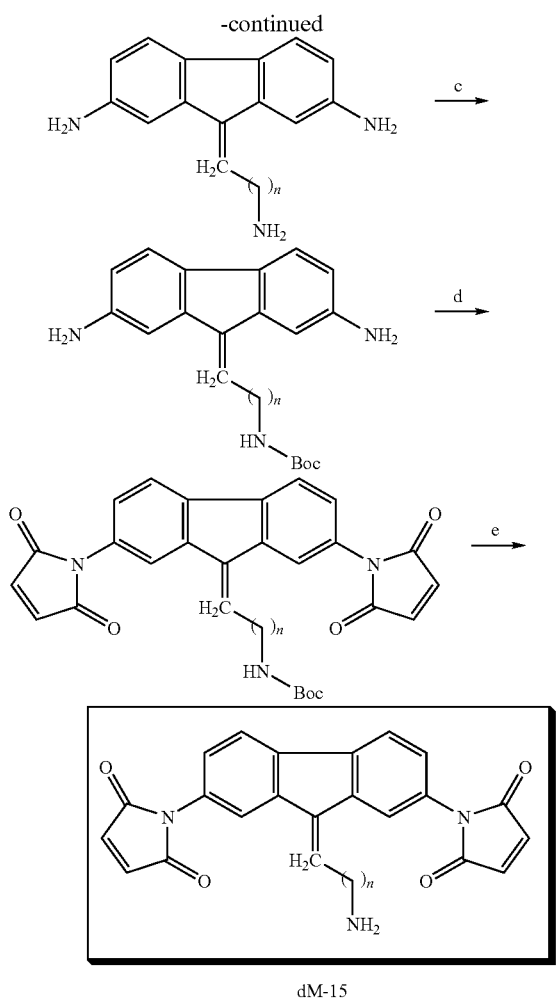

dM-15

(a) Wittig reaction with Ph₃PCH(CH₂)ₙNH₂
(b) H₂/Pd/C, 150 psi, THF
(c) (Boc)₂O, Et₃N, MeOH at 0° C.
(d) (i) maleic anhydride, CHCl₃, reflux,
    (ii) Ac₂O, AcONa, 100° C.
(e) TFA, anisole, CH₂Cl₂ at 0° C.

Fluorescence

In order to understand how the thiol addition reactions of fluorogens 4 and 13 result in the formation of more fluorescent products, it is instructive to consider how the maleimide groups quench fluorescence. It has been suggested that their π bonding orbitals are stabilized by the extended conjugation of a maleimide group. As such, in molecules bearing maleimide groups, the molecular orbital of highest energy (HOMO) corresponds to the lone pair electrons of the maleimide carbonyl group and the lowest unoccupied orbital (LUMO) is its antibonding π* orbital. Excitation leads to an excited state from which radiative relaxation is formally forbidden for the π*→n transition; fluorescence is quenched and relaxation takes place in a non-radiative fashion. The thiol addition reaction of the maleimide group leads to a loss of conjugation, destabilization of the carbonyl group and inversion of the energy levels of the π and n molecular orbitals. In the resulting thioalkyl succinimide group, radiative relaxation from the excited state can take place though the formally allowed π*→π transition, restoring fluorescence of the aromatic core (Scheme 9).[15,16]

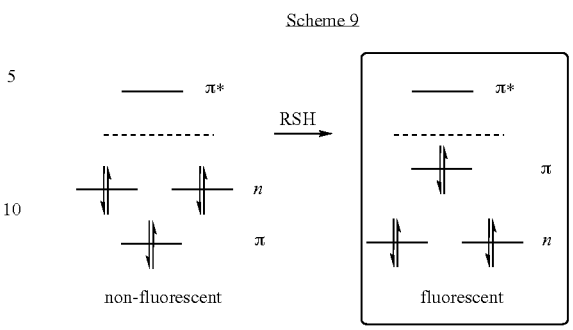

Scheme 9

For the application of this fluorogenic reaction to the detection of thiols and dithiols, two important criteria are the fluorescence intensity of the thiol addition product and the ratio of its fluorescence compared to its parent fluorogen. We studied the effect of electron withdrawing and donating substituents on these criteria by preparing the derivatives of fluorogen 4 shown in Scheme 1. Fluorogen 5, bearing an electron withdrawing ester group, was prepared according to a protocol similar to that used for fluorogen 4, but using an ester-substituted maleic anhydride derived by oxidation of dimethyl L-tartrate according to a published procedure.[31] Fluorogen 6 bears an electron donating methyl group and was obtained in similar yield by adaptation of the standard literature protocol,[25] using citraconic anhydride. The reaction of 5 and 6 with ethanethiol in DMSO led to the formation of thiol adducts 8 and 9, whose fluorescence was characterized as shown in Table 1. Even from this small series, certain tendencies are apparent. Increasing the electron donating capacity of the substituent appears to have a significant effect on the absorbance maximum corresponding to the wavelength of excitation, increasing by 37 nm from 8 to 9. Although the emission wavelength increases very slightly over the same series, the net effect on the Stokes shift is a significant decrease with increasing electron donating capacity of the substituent. A slight increase in the ratio of fluorescence intensity (before and after reaction with two equivalents of ethanethiol) was also observed to follow increasing substituent electron donating capacity, as expected.[32] (In light of this trend, the methoxy derivative of 4 was also prepared,[33] but the thiol addition reaction was apparently suppressed upon introduction of such a strong electron donating group on the maleimide group, and no thiol adduct was formed.) While these substituent effects on fluorescence may provide data for detailed spectroscopic discussion outside the objectives of this work, they do not offer any appreciable improvements with respect to the criteria mentioned above.

TABLE 1

Effect of substituents on the spectral properties of derivatives of fluorogen 4 and their corresponding ethanethiol adducts in DMSO.

| Fluorogen/ adduct | R = | $\lambda_{exc}$ (nm) | $\lambda_{em}$ (nm) | Stokes shift (nm) | $I_F$ Ratio[b] |
|---|---|---|---|---|---|
| 4/7 | H | 360 | 370-600 (450) | 90 | 3.0 |
|  |  | 351 |  | 99 |  |
| 5/8 | CO₂Me | 332 | 360-600 (447)[a] | 115 | 2.7 |
|  |  | 336 |  | 121 |  |

TABLE 1-continued

Effect of substituants on the spectral properties of derivatives of fluorogen 4 and their corresponding ethanethiol adducts in DMSO.

| Fluorogen/adduct | R = | $\lambda_{exc}$ (nm) | $\lambda_{em}$ (nm) | Stokes shift (nm) | $I_F$ Ratio[b] |
|---|---|---|---|---|---|
| 6/9 | CH$_3$ | 373 | 370-600 (455) | 82 | 3.6 |
|  |  | 373 |  | 82 |  |

[a]Wavelength corresponding to center of Full Width at Half Maximum of emission band.
[b]Calculated by the ratio of the areas under the fluorescence emission bands of the fluorogens and their respective thiol adduct products.

An alternative strategy for significantly altering the desired fluorescent properties involves replacement of the fluorophore core. Fluorophore 15 reacts with ethanethiol in DMSO to form a dithiolated adduct (16) that is more fluorescent than 15 by a factor of 31 (Table 2) and easily detected at micromolar concentrations. However, 15 proved to be insoluble in water, even upon the addition of up to 10% DMSO, rendering its practical application to the labeling of proteins problematic. Fluorophore 20 was prepared as a more polar naphthalene derivative and was found to be soluble in aqueous solutions containing as little as 5% DMSO. The adduct resulting from reaction with ethanethiol (21) was also easily detected at micromolar concentrations and found to fluoresce 8.5 times more intensely than 20. Comparison of the fluorescent properties[34] of the four different parent fluorogens (and their corresponding thiol adducts) studied herein (see Table 2) substantiates our retention of compounds 13 and 20 as candidates for further tests with proteins.

TABLE 2

Effect of fluorophore core on the spectral properties of fluorogens 4, 13, 15 and 20 and their corresponding ethanethiol adducts.

| Fluorogen/adduct | $\lambda_{exc}$ (nm) | $\lambda_{em}$ (nm) | Stokes shift (nm) | $I_F$ Ratio[c] | $\varphi^d$ |
|---|---|---|---|---|---|
| 4/7 | 360 | 370-600 (450)[b] | 90 | 3.0 | 4.55 × 10$^{-5}$ |
|  | 351 |  | 99 |  | 0.027 |
| 13/ | 384 | 400-550 (460) | 76 | 5.2 | 0.006 |
| 14 | 384 |  | 76 |  | 0.223 |
| 15[a]/ | 328 | 340-500 (391) | 63 | 31 | 1.70 × 10$^{-3}$ |
| 16 | 328 |  | 63 |  | 0.128 |
| 20/ | 511 | 525-650 (578) | 67 | 8.5 | N/A[e] |
| 21 | 511 |  | 67 |  | N/A[e] |

[a]Compounds 4, 13 and 20 were characterized in 10:90 DMSO:water, but it was necessary to use neat DMSO to dissolve compound 15, to allow comparison of all of the fluorogens.
[b]Wavelength corresponding to center of Full Width at Half Maximum of emission band.
[c]Calculated by the ratio of the areas under the fluorescence emission bands of the fluorogens and their respective thiol adduct products.
[d]Calculated by the rapid approximation method published in reference 34.
[e]Overlap between the excitation band of fluorescein and the emission band of derivatives of 20 prevented the typical relative determination of quantum yield as given in reference 34.

Finally, the effects of pH and temperature on fluorescence intensity were studied using compound 7, the thiol adduct of fluorogen 4. Between pH 6.2 and 7.2, a negligible difference in fluorescence intensity was observed. From pH 7.2 to 8.2, a slight decrease of less than 20% was observed. It is difficult to attribute this slight difference to a pH effect, as opposed to the small quench typically observed in anionic solvents.[32] In any case, the difference is relatively small and suggests that at pH near neutrality, conditions under which the labeling reaction will ideally be employed, the fluorescence appears to be insensitive to slight variations in pH. A similar lack of sensitivity was observed with respect to changes in temperature. From 25 to 40° C., the fluorescence of 7 was found to vary negligibly. From 40 to 80° C., fluorescence was found to decrease by less than 10%, potentially due to partial decomposition of the thiol adduct product. These results also suggest that for the application of this labeling method under typical conditions, such as room temperature or 37° C., slight variations in temperature would not have a significant effect on the observed fluorescence.

Protein Design and Expression

As mentioned in the introduction, an α-helical protein was designed to bear two cysteine residues, separated by a distance complementary to that between the maleimide groups of the designated fluorogen. The protein chosen as a starting point for this design was the C99S mutant of a fragment of Fos,[21] a known α-helical protein[22] whose recombinant expression has been published.[23] Site-directed mutagenesis was then performed[20,35] to introduce a cysteine residue (L56C), separated by two turns of the α-helical motif from the native Cys49, positioning the protein's only two thiol groups approximately 10 Å apart.[36] Although at higher concentrations, Fos is known to form a homodimer,[22] the distance between the intermolecular cysteine residues in this putative homodimer would render their reaction with a single fluorogen molecule impossible. The plasmids encoding for both the monocysteine and dicysteine mutants of Fos (mCys-Fos and diCys-Fos) were then sub-cloned into a pQE32 expression vector that adds an N-terminal His-tag, facilitating the subsequent purification of these test proteins, for subsequent in vitro tests, by immobilized nickel ion chromatography after overexpression in XL1-blue *E. coli* cells.

EXAMPLE 1

Protein Labeling In Vitro

Purified mCys-Fos and diCys-Fos were then tested in vitro for their ability to react with fluorogens 13 and 20. After incubation of 0.242 mM protein with 0.5 mM of 20 or 0.05 mM of 13 at 25° C. overnight, glycerol was added and the reaction mixtures were analyzed by SDS-PAGE using UV illumination and then Coomassie blue staining. From the resulting gel shown in FIG. 5, it is clear that even under these extended reaction conditions, diCys-Fos is efficiently fluorescently labeled by either fluorogen, whereas mCys-Fos is not. Furthermore, the fluorogens tested do not react with two equivalents of mCys-Fos, as evidenced by the absence of a band corresponding to the molecular weight of the expected covalent dimeric protein-fluorogen adduct. This selectivity for reaction with one equivalent of dithiol, rather than two equivalents of monothiol, was also observed for small organic thiols and dithiols, as discussed above. Tsien has also remarked on this kinetic advantage in the reaction of dithiols versus monothiols with bisarsenical fluorogens.[9] Apparently, the entropic advantage realized by positioning both thiol groups in one protein molecule leads to the reaction with dithiol being kinetically favored. This selectivity is of critical importance for the use of this method for in vivo labeling applications.

Figure 6:
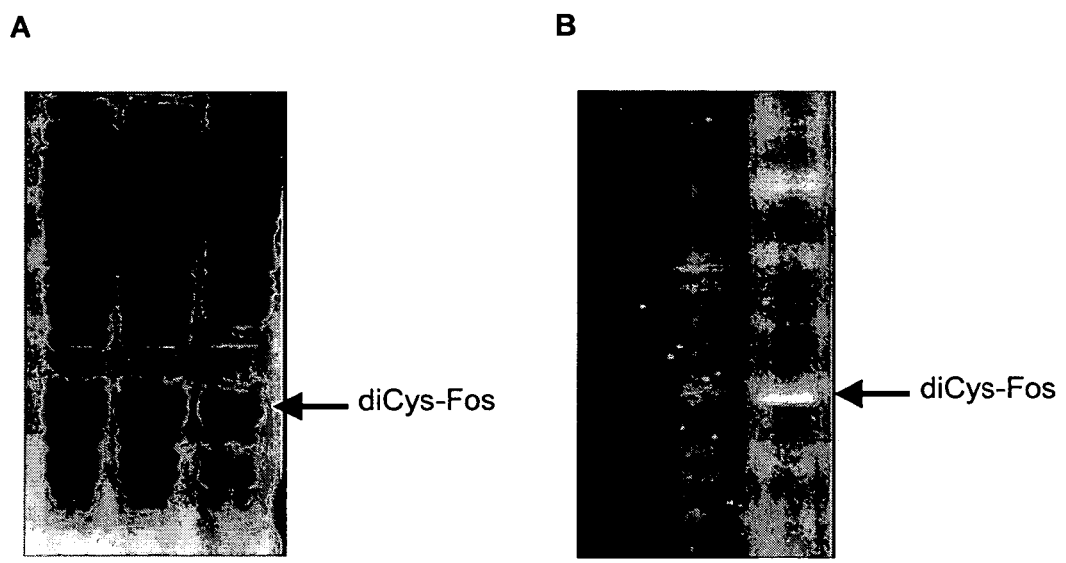
FIG. 6: SDS-PAGE analysis of the reaction of fluorogens 13 and 20 with the lysate of XL-1 blue *E. coli* cells expressing diCys-Fos: Lane 1: 5 μL lysate; lane 2: 5 μL lysate+13 (0.05 mM); lane 3: 5 μL lysate+20 (0.5 mM). A) Coomassie blue staining; B) fluorescence (UV excitation)

The specificity of the dithiol addition reaction of 20 with diCys-Fos in the presence of other proteins was also confirmed through a simple in vitro experiment. The lysate of *E. coli* cells expressing diCys-Fos was allowed to react with 20 overnight at 25° C. prior to analysis by SDS-PAGE. The resulting gel, shown in FIG. 6, demonstrates the selectivity of 20 for its designated target protein in the presence of all other cytosolic proteins, confirming the apparent rarity of the random occurrence of appropriately positioned Cys residues in native proteins.[9]

EXAMPLE 2

Protein Labeling In Vivo

Figure 7:
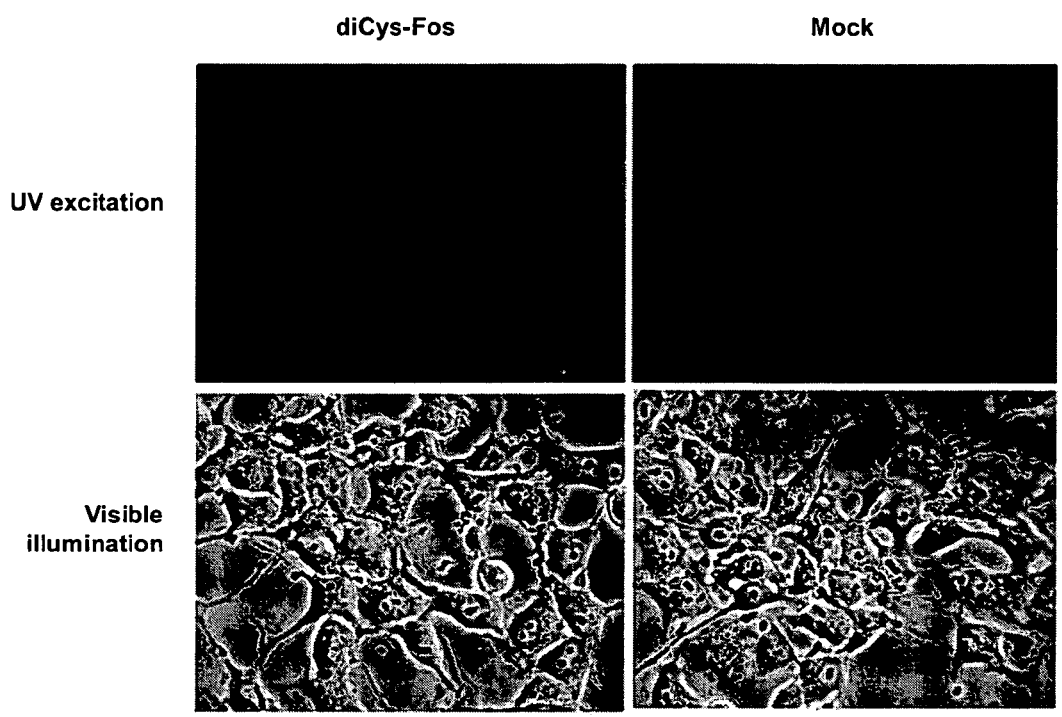
FIG. 7: Fluorescent labeling of diCys-Fos in COS cells by 10 μM fluorogen 20 after 20 minutes.

The ultimate proof of principle for this method is its successful application to labeling a specific protein in living eukaryotic cells. To test for this potential, our diCys-Fos probe protein was genetically fused to RBD, the Ras-binding domain of Raf, and COS cells were then transfected with the expression plasmid for this fusion protein. A solution of 20 was then added to cultures of COS cells expressing diCys-Fos as well as mock COS cells transfected with an empty expression plasmid. At a final concentration of 10 µM 20, a significant difference in fluorescence was observed after 20 minutes of incubation at room temperature.[20] As shown in FIG. 7, cells expressing diCys-Fos display the blue fluorescence typical of dithiol adducts of 20 far more than cells not expressing diCys-Fos, confirming the cell permeability of 20, the specificity of its reaction with our helical probe protein and the viability of this labeling method in vivo.

Figure 8:
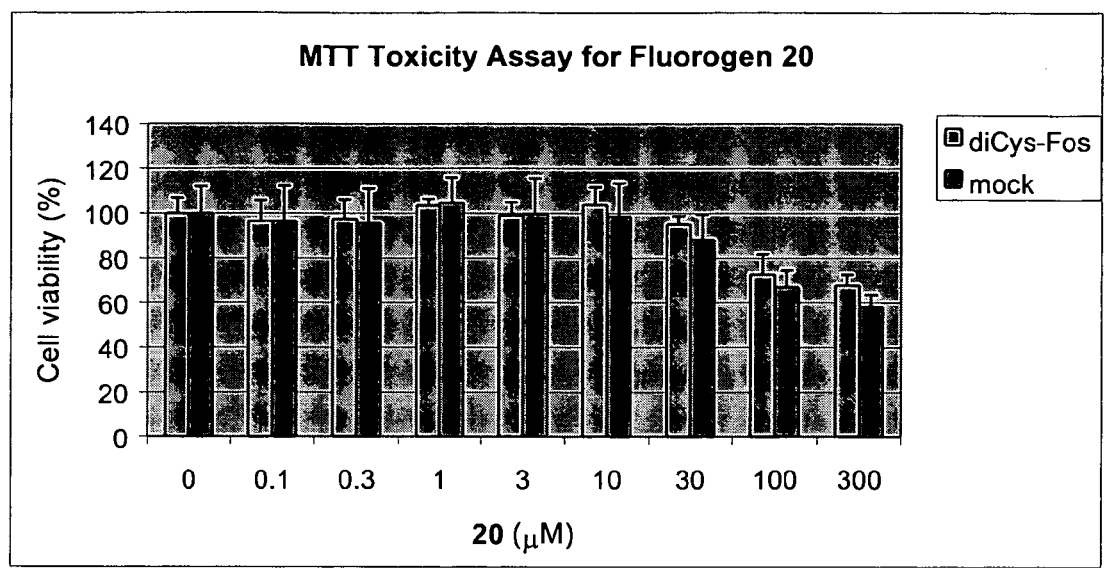
FIG. 8: Low toxicity of fluorogen 20 administered to COS cells, up to limit of solubility, at concentrations 30 times greater than required for effective visualization of labeling of diCys-Fos

Finally, we wished to determine if fluorogens such as 13 and 20 were cytotoxic. Using the MTT and PI assays, the percentage of viable COS cells was found to be unaffected by concentrations of up to 30 µM 20. Furthermore, even at 300 µM 20, the limit of its solubility in cell culture, 70% of COS cells were still viable (FIG. 8). Compared to other fluorogens currently employed, containing arsenic and requiring co-administration of antidote dithiols,[9] it is hardly surprising that our fluorogens are far less cytotoxic, since they do not contain harmful heavy metals. The convenience of the application of this fluorescent labeling method is obvious from the low cytoxocity of 20, even at concentrations 30 times greater than those necessary for efficient labeling.

EXAMPLE 3

Second and Third Generation Fluorophores

Figure 9:
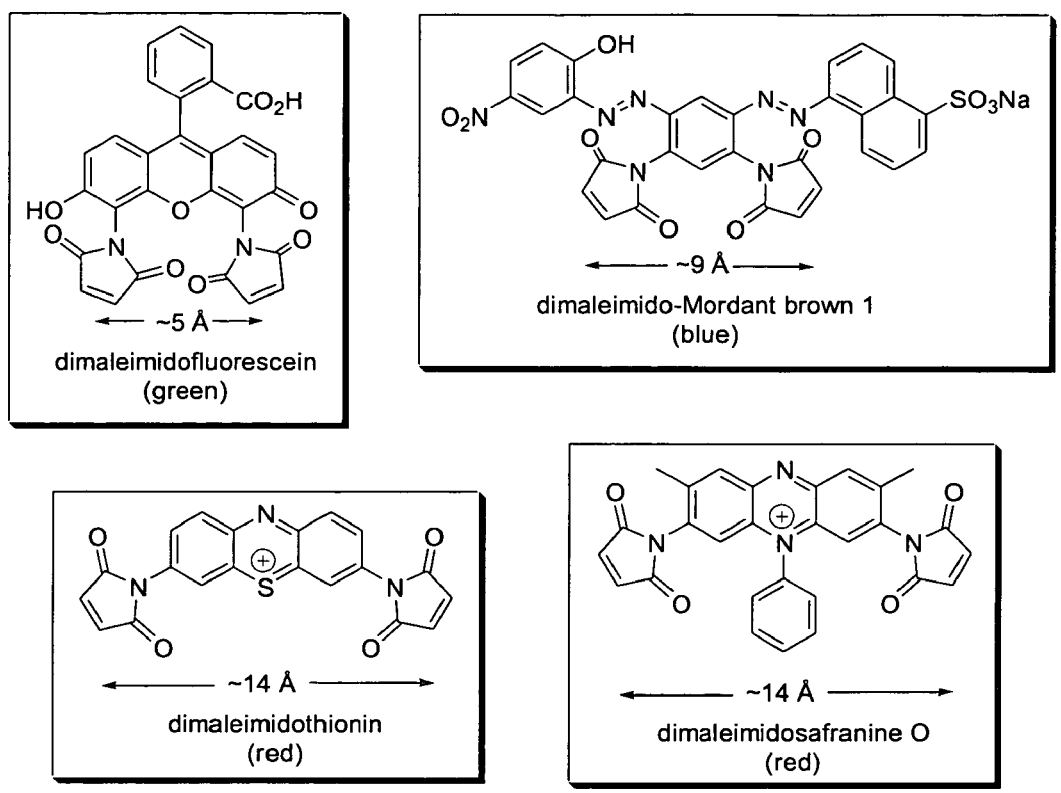
FIG. 9: Some representative fluorogens.

In many respects, our previous results have already validated our fluorescent assay. For example, we have demonstrated the fluorogenic reaction of dimaleimide derivatives of coumarine and naphthalene fluorophores; other fluorogens are now being synthesized, along the same general synthetic pathways as those shown in Schemes 1-4. These second- and third-generation fluorogens will be evaluated for their solubility and cell permeability, as well as their fluorescent properties. These properties include the enhanced fluorescent intensity of their dithiolated adducts, their lack of fluorescence prior to their thiol addition reactions and the wavelengths of their fluorescent emission bands. The latter characteristic is important in order to allow the facile detection of their fluorescent thiolated forms against the background fluorescence of intracellular biomolecules. Several candidate fluorogens that may satisfy these criteria have been identified for synthesis, some of which are shown in FIG. 9.

Finally, if the intracellular concentration of our fluorogens needs to be increased for in vivo application, we will further elaborate their structures according to commonly used strategies. For example, we will add esters or carbohydrate functional groups, since they can be hydrolyzed or phosphorylated respectively within the cell, leading to charged derivatives that can no longer exit through the cell membrane, resulting in their intracellular accumulation.

EXAMPLE 4

Figure 10:
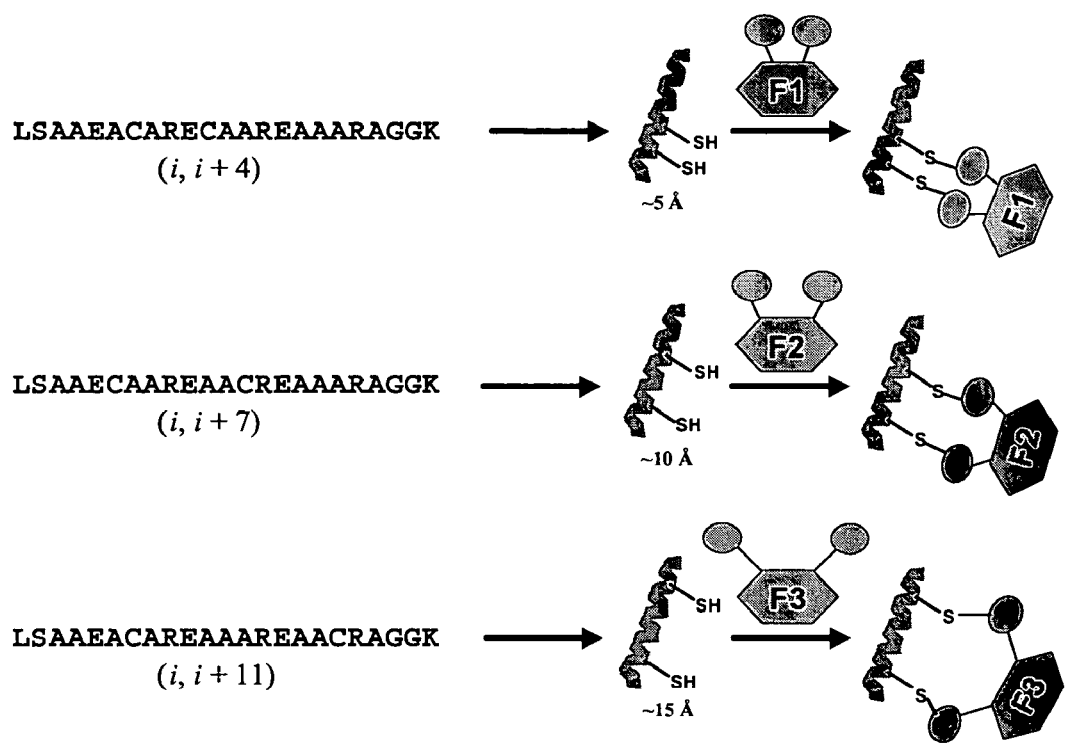
FIG. 10: Sequences, intercysteine distances and proposed specificity of three diCys probe proteins

Fluorogen-Induced Peptide Folding for Improved Protein Labeling and Biological Specificity The other half of this fluorescent labeling technique, the probe protein sequence, can be refined. Although Fos was chosen as an α-helical probe protein for initial tests, its potential intracellular biological activity and ability to form (weak) homodimers[22] make it far from optimal. Small monomeric α-helical proteins have been designed de novo, in order to minimize the likelihood that they would display adventitious biological activity (FIG. 10). The short helical peptides recently synthesized by Woolley,[37] based on helical peptide sequences previously elaborated in the literature,[38,39] served as an excellent starting point for our designs, since they already contain two cysteine residues. N- and C-termini can be added according to common N- and C-cap sequences already published.[40] The positioning of the cysteine residues within our probe sequences can also be optimized to minimize their perturbation of the expected helicity predicted by the AGADIR algorithm.[41,42] Finally, the final sequences of these probe proteins will be optimized by screening libraries[43] of recombinant probe proteins containing random mutations that may improve their solubility, reactivity and selectivity.

Optimization and Application of In Vivo Protein Labeling

The second specific objective of the development of this method is its application to the specific labeling of proteins in vivo. Again, our preliminary results have already demonstrated the feasibility of this application in mammalian cells expressing a fusion protein containing the probe protein sequence. However, we can optimize the probe protein-fluorogen pairs by exploring the selectivity of the reaction of given fluorogens (FIG. 9) with diCys α-helical proteins of different distance between cysteine residues. For example, we propose that fluorogens having maleimide groups separated by ~5 Å, will fluoresce selectively upon reaction with the de novo i,i+4 diCys probe proteins, whereas the i,i+11 diCys probe sequence would be selectively fluorescently labeled by fluorogens bearing maleimide groups separated by ~15 Å (see FIG. 10).

Figure 11:
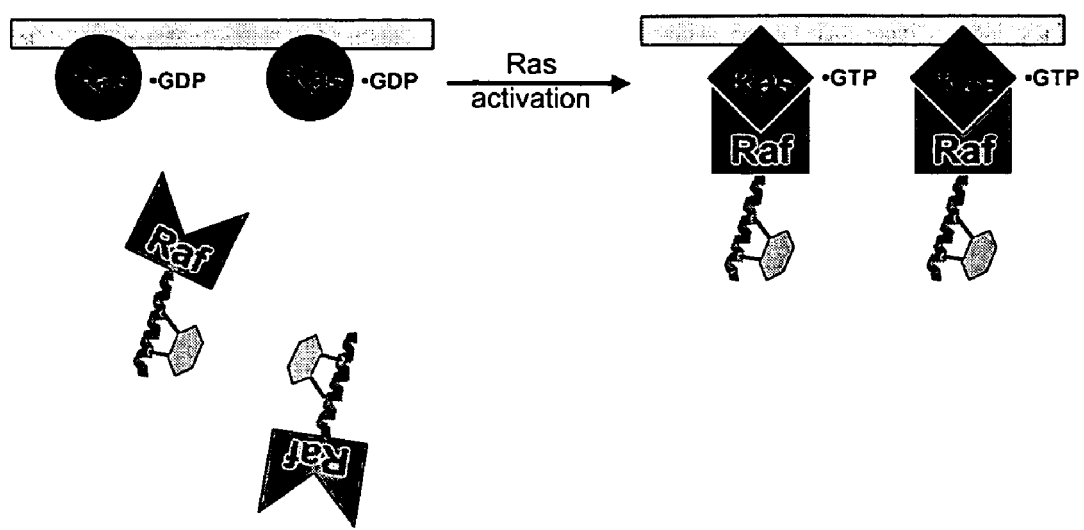
FIG. 11: Specific labeling and localization of RBD of Raf through the use of fluorogens that react specifically with complementary α-helical probe protein sequences

The potential for the application of this method to the quantitation and localization of intracellular proteins can be explored through the use of a specific test system, namely that of the Ras signaling protein. Ras proteins are monomeric GTPases that regulate cell growth by controlling signaling events primarily at the interior cell membrane, although their possible localization in other organelles remains a current area of research.[44,45] When Ras is activated by cell growth factors, involving the exchange of its GDP ligand with GTP, it undergoes a conformational change that leads to a high-affinity interaction with Raf through its Ras-binding domain (RBD). The RBD of Raf has been fluorescently labeled with GFP and its localization in mammalian cells has been observed to be dependent on the activation state of Ras;[46] in its active state, Ras recruits Raf to where it is bound on the interior cell membrane. We express Raf as a fusion protein with one of our diCys α-helical probe proteins, permitting it to be specifically labeled in the cell after addition of an appropriate fluorogen (FIG. 11). Fluorescence microscopy of the cells then reveals the localization of Raf in the cytosol or various organelles. Upon, subsequent activation of Ras through the addition of a growth factor, we are able to follow the translocation of Raf, to the interior cell membrane or to other organelles, providing information on Ras-Raf-mediated signal transduction. Furthermore, these results can be compared to those obtained using the GFP-Raf fusion protein,[46] permitting a critical comparison of the two methods and a potential evaluation of the possible perturbation of the biological activity of Ras caused by the mass and steric bulk of the attached GFP. In general, this application could demonstrate the scope of the application of our novel fluorogenic method for the specific labeling and monitoring of the life cycle of any cellular protein.

EXAMPLE 5

Multiplex Labeling and Detection of Protein-Protein Interactions

The selectivity of the reactions of certain helical probe/fluorogen pairs, described in Example 4 allow us to label simultaneously different cellular proteins with different fluorophores, permitting not only the distinction between the different localization patterns, but also the study of their potential interaction using Fluorescence Resonance Energy Transfer. Essentially, in the phenomenon known as FRET, one excited (donor) fluorophore transfers its energy to a second (acceptor) fluorophore within close proximity, leading ultimately to higher wavelength emission from the acceptor fluorophore.[47] In particular, the donor/acceptor fluorophore pair of fluorescein/rhodamine has been employed to detect events that bring biomolecules within 10-100 Å of each other, including protein-protein interactions.[48] Different mutants of GFP have also been applied to this method, where excitation of the donor GFP leads to emission from the acceptor fluorescent protein.[8] Not only does our method offer a less intrusive small molecule approach compared to the use of a large GFP protein, but it also permits the specific labeling of target proteins and the flexible modification of the fluorophores used, allowing the facile tuning of fluorophores in order to maximize the observed FRET process.

Figure 12:
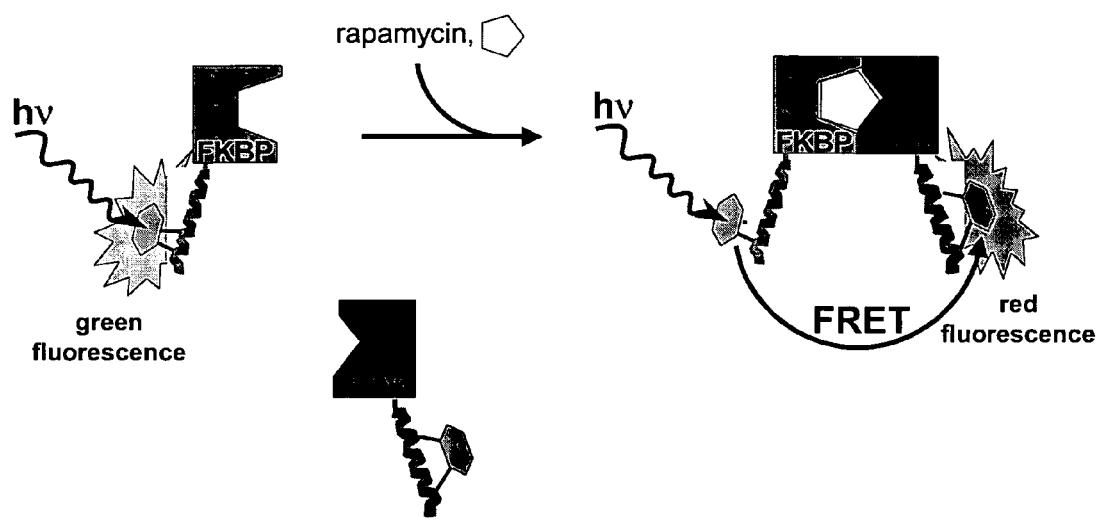
FIG. 12: Rapamycin-mediated interaction of FKBP and TOR, and resulting FRET phenomenon, to be detected through their selective labeling with different fluorogen/probe protein pairs.

The system used to test for this application is that of FKBP and TOR. These proteins form a stable heterodimer (whose structure is known[49,50]), but only in the presence of the antibiotic rapamycin. We express FKBP and TOR as fusion proteins with different helical probe sequences that will be specifically recognized by different fluorogens designed for their ability to participate in the FRET process. In the presence of rapamycin, the fluorescently labeled FKBP and TOR fusion proteins form their typical heterodimer complex, bringing their fluorophores into sufficient proximity of each other to allow a FRET interaction (FIG. 12). The observed FRET fluorescence should show dependence on the concentration of rapamycin. This test system has been used extensively for the development of other techniques for the detection of protein-protein interactions,[51] and allows assessment of the scope and limitations of the application of our novel fluorogenic method.

Our results clearly demonstrate the proof of principle for our novel fluorogenic method for the specific labeling of proteins in vivo. The thoroughness of our bioorganic approach to the study of protein chemistry has tremendous potential for the notable advancement of our general comprehension of protein reactivity inside living cells. Moreover, in its ultimate application to the elucidation of dynamic protein localization and function, this technique will represent an enormous contribution to the vital field of proteomics and chemical biology. Furthermore, it could provide an important breakthrough in the high-throughput genomic screening leading to the discovery of protein-protein interactions of biological and medical importance. In summary, the method described herein has the potential to serve as a powerful tool for elucidating the roles of a myriad of gene products.

Experimental Section

Materials

The following material were obtained from Aldrich and were used without further purification: 2-hydroxy-5-nitrobenzaldehyde, N-acetylglycine, maleic anhydride, p-nitrophenylacetic acid, L-aspartic acid dimethyl ester hydrochloride, citraconic anhydride, dimethyl L-tartrate, dimethyl malonate. All reactions were carried out under an atmosphere of dry nitrogen employing conventional bench-top techniques except for reactions with thiols. $^{13}$C-NMR and $^{1}$H-NMR spectra were recorded on AMXR400 or AMX300 spectrometers and were referenced to the residual proton or $^{13}$C signal of the solvent. Mass spectra were determined by FAB+ ionization on an AutoSpecQ spectrometer at the Regional Mass Spectrometry Centre at the Université de Montréal. Infrared spectra were recorded on a Perkin-Elmer (FTIR) spectrometer. Melting points (uncorrected) were determined on a Unimelt Tomas-Hoover or on a Gallenkamp meting point apparatus. Fluorescence spectra were recorded using a Varian Cary Eclipse fluorimeter and gel electrophoresis was carried out on a SpectraPhoresis 100 apparatus.

Methods

Synthesis

3-Acetamido-6-nitrochromen-2-one (1)

A dry 100-mL round bottomed flask was charged with 7.11 g (42.5 mmol) of 2-hydroxy-5-nitrobenzaldehyde. To this flask were then added N-acetylglycine (4.98 g, 42.5 mmol) and acetic anhydride (40.1 mL, 0.43 mol). In small aliquots, 1.71 g (42.5 mmol) of sodium hydride (60% dispersion in mineral oil) was added to the flask. Reactants were observed to dissolve and after 2-5 minutes, precipitation occurred. The reaction mixture was stirred for 20 h and 7.11 mL of water were added. Following the addition of 43 mL acetic acid, the mixture was cooled to 4° C. for 4 h. The resulting precipitate was filtered and washed liberally with cold glacial acetic acid. The acetic acid was then removed as an azeotrope upon addition of 250 mL toluene and rotary evaporation to dryness, three times. The final residue was dried under vacuum to give product 1 as a beige powder (6.40 g, 25.8 mmol) in a yield of 61%. mp 277-279° C. (lit: 278° C.) FTIR (KBr) (cm$^{-1}$) 3350, 3050, 1710, 1680, 1600, 1500, 1420, and 1335. $^{1}$H-NMR (DMSO-d$_6$): δ (ppm) 9.93 (s, 1H), 8.76 (s, 1H), 8.73 (d, J=2.5 Hz, 1H), 8.28 (dd, J=2.8 Hz, J=9.1 Hz, 1H), 7.60 (d, J=9.1 Hz, 1H), 2.19 (s, 3H). $^{13}$C-NMR (DMSO-d$_6$): δ (ppm) 171.47, 157.69, 145.07, 127.11, 124.96, 124.52, 122.79, 121.52, 118.26, 25.00. HRMS expected: 249.05240; found: 249.05339. Elemental analysis for $C_{11}H_8N_2O_5$, expected: C, 53.23; H, 3.25; N, 11.27; found: C, 53.19; H, 3.34; N, 11.06.

3-Acetamido-6-aminochromen-2-one (2)

Palladium 10 wt % on activated carbon (0.322 g, $^{1}/_{10}^{th}$ the mass of 1) was placed in a 1-L round-bottom flask and the flask was purged with nitrogen. A solution of sodium borohydride (1.21 g, 32.9 mmol) in 22.6 mL water was added drop-wise. A suspension of compound 1 (3.20 g, 12.9 mmol)

in methanol (775 mL) was then added over a two hour period and allowed to stir at room temperature an additional 30 min, when the reaction mixture was filtered through Celite and the solvent was removed by rotary evaporation. Water (750 mL) was added to the residue and the solution was cooled to 4° C. for 20 h. The resulting precipitate was filtered and rinsed with cold distilled water. The solid was recrystallized from ethanol to give 2 as a yellow solid (1.59 g, 7.3 mmol) in 57% yield. mp 250-252° C. (lit 252-253° C.). FTIR (KBr) (cm$^{-1}$): 3410, 3310, 1700, 1650, 1630. $^1$H-NMR (DMSO-d$_6$): δ (ppm) 9.65 (s, 1H), 8.40 (s, 1H), 7.10 (dd, J=9.1 Hz, J=2.7 Hz, 1H), 6.73 (d, J=9.1 Hz, 1H), 6.68 (d, J=2.7 Hz, 1H), 5.19 (bs, 2H), 2.14 (s, 3H). $^{13}$C-NMR (DMSO-d$_6$): δ (ppm) 171.12, 158.78, 146.92, 142.52, 125.26, 124.98, 120.82, 117.54, 117.15, 110.66, 24.93. HRMS expected, 219.07770; found, 219.07697. Elemental analysis for $C_{11}H_{10}N_2O_3$: expected: C, 60.55; H, 4.62; N, 12.84; found: C, 60.15; H, 4.50; N, 12.62.

3,6-Diaminochromen-2-one (3)

To a solution composed of 12.63 mL of 12 M hydrochloric acid in 6.32 mL ethanol was added 0.919 g (4.2 mmol) of compound 2. The solution was heated to reflux for 30 min and then cooled to 4° C. overnight. The resulting precipitate was removed by filtration and dissolved in a minimal volume of distilled water. The solution was neutralized by addition of 25% ammonium hydroxide and cooled at 4° C. for three hours. The resulting precipitate was removed by filtration and recrystallized from water to give a yellow compound (3) (0.484 g, 2.7 mmol) in 65% yield. mp 183-186° C. (lit: 183-184° C.). FTIR (KBr) (cm$^{-1}$): 3420, 3340, 1690, 1635. $^1$H-NMR (DMSO-d$_6$): δ (ppm) 6.95 (d, J=8.5 Hz, 1H), 6.56 (s, 1H), 6.49 (d, J=2.4 Hz, 1H), 6.46 (dd, J=10.0 Hz, J=2.6 Hz, 1H), 5.48 (bs, 2H), 5.00 (bs, 2H). $^{13}$C-NMR (DMSO-d$_6$): δ (ppm) 159.95, 146.50, 141.19, 134.13, 123.04, 116.75, 113.70, 109.30, 108.42. HRMS expected: 177.05920; found: 177.05979.

3,6-Dimaleimidylchromen-2-one (4)

Diamine 3 (200 mg, 1.14 mmol) and maleic anhydride (335 mg, 3.42 mmol) were placed in a dry 50-mL round bottom flask. Chloroform (11.5 mL) was added and the solution was heated to reflux for 20 h. The mixture was then filtered and the recovered solid was rinsed liberally with chloroform and then dried under vacuum. To this solid was added acetic anhydride (9 mL, 96 mmol) and sodium acetate (35 mg, 0.427 mmol) and the reaction was stirred vigorously for another 30 min. The mixture was then cooled to 4° C. for 4 h and filtered. The beige solid thus obtained was dried over vacuum to give compound 4 in 20% yield (76 mg, 0.226 mmol). mp: >296° C. (dec). FTIR (KBr) (cm$^{-1}$): 1700, 1620. $^1$H-NMR (CDCl$_3$): δ (ppm) 7.78 (s, 1H), 7.66 (dd, J=9.8 Hz, J=2.5 Hz, 1H), 7.63 (d, J=2.5 Hz, 1H), 7.50 (d, J=8.7 Hz, 1H), 6.93 (s, 2H), 6.91 (s, 2H). $^{13}$C-NMR (DMSO-d$_6$): δ (ppm) 1699.99, 169.06, 156.80, 151.50, 143.62, 135.82, 134.89, 131.61, 128.63, 127.11, 118.60, 118.13, 117.58. HRMS: expected, 337.04630; found, 337.04605.

3,6-Di-(3'-methoxycarbonylmaleimidyl)chromen-2-one (5)

To a suspension of diamine 3 (268 mg, 1.52 mmol) in dry chloroform (15.4 mL) was added α-carbomethoxymaleic anhydride (712 mg, 4.56 mmol). The solution was heated to reflux for 20 h, then cooled to room temperature and filtered. The solid thus obtained was rinsed liberally with chloroform and dried under reduced pressure. It was then added to 12 mL acetic anhydride and 47 mg of sodium acetate (0.56 mmol). The mixture was then heated to 100° C. for 90 min and then allowed to cool to room temperature for 24 h. The resulting precipitate was recovered by filtration and rinsed with water, giving the desired product 5 in 22% yield (151 mg, 0.33 mmol). mp>230° C. (dec). FTIR (KBr) (cm$^{-1}$): 1720, 1670. $^1$H-NMR (DMSO-d$_6$): δ (ppm) 8.24 (s, 1H), 8.04 (s, 2H), 7.66 (dd, J=8.97 Hz, J=2.43 Hz, 1H), 7.42 (d, J=8.96 Hz, 1H), 7.40 (d, J=2.42 Hz, 1H), 4.04 (s, 3H), 4.00 (s, 3H). $^{13}$C-NMR (DMSO-d$_6$): δ (ppm) 171.02, 163.38, 132.09, 159.92, 145.83, 142.80, 142.31, 135.32, 128.06, 124.83, 120.92, 119.92, 119.27, 117.16, 48.83. HRMS expected for $C_{21}H_{12}N_2O_{10}$: 452.049194; found: 452.049086.

3,6-Di-(3'-methylmaleimidyl)chromen-2-one (6)

To a suspension of diamine 3 (268 mg, 1.52 mmol) in 15.4 mL of dry chloroform was added citraconic anhydride (410 µL, 4.56 mmol). The mixture was heated to reflux for 20 h. The mixture was cooled to room temperature and filtered, and the recovered solid was rinsed well with chloroform. After drying, it was added to a solution of sodium acetate (47 mg, 0.56 mmol) in acetic anhydride (12 mL). The mixture was heated to 100° C. for 90 min and then cooled to room temperature and allowed to stand for 24 h. The resulting precipitate was then filtered and rinsed with water to give the desired product 6 in 20% yield (147 mg, 0.3 mmol). mp>230° C. (dec). FTIR (KBr) (cm$^{-1}$): 1720, 1654. $^1$H-NMR (CDCl$_3$): δ (ppm) 8.52 (s, 1H), 7.88 (d, J=2.29 Hz, 1H), 7.63 (s, 1H), 7.52 (dd, J=9.26 Hz, J=2.29 Hz, 1H), 7.45 (s, 1H), 7.34 (d, J=8.83 Hz, 1H), 2.07 (d, J=6.92 Hz, 3H), 1.91 (d, J=7.02 Hz, 3H). $^{13}$C-NMR (DMSO-d$_6$): δ (ppm) 170.00, 169.02, 158.90, 146.22, 137.32, 126.04, 122.06, 120.43, 118.24, 117.16, 24.80. HRMS expected for $C_{19}H_{12}N_2O_6$: 364.069536; found: 364.069312.

3,6-Di(3'-ethylthiosuccinimidyl)chromen-2-one (7)

To a suspension of 4 (40 mg, 0.12 mmol) in 3 mL dry chloroform was added 27 µL (0.36 mmol) of ethanethiol. The solution was stirred at room temperature for 12 h, then concentrated under reduced pressure and purified by flash chromatography (30:70 EtOAc:hexane). Compound 7 was thus obtained as a yellow solid in 85% yield (47 mg, 0.10 mmol). mp 128-131° C. FTIR (KBr) (cm$^{-1}$): 3000, 1700, 1620, 600. $^1$H-NMR (CDCl$_3$): δ (ppm) 7.46 (m, 2H), 7.42 (d, J=11.0 Hz, 1H) 7.39 (s, 1H), 3.90 (d, J=5.6 Hz, 1H), 3.88 (d, J=5.6 Hz, 1H), 3.35 (q, J=9.7 Hz, 2H), 2.94 (m, 2H), 2.80 (m, 2H), 2.69 (d, J=5.6 Hz, 1H), 2.64 (d, J=5.6 Hz, 1H), 1.29 (t, J=8.0 Hz, 6H). $^{13}$C-NMR (CDCl$_3$): δ (ppm) 175.20, 173.42, 167.90, 155.98, 151.07, 136.55, 130.14, 128.85, 128.25, 125.39, 118.72, 117.35, 38.72, 35.96, 26.04, 20.40, 14.03. HRMS calculated: 461.08510; found: 461.08491. Elemental analysis for $C_{21}H_{20}N_2O_6S_2$ expected: C, 54.77; H, 4.38; N, 6.08; S, 13.92; found: C, 54.49; H, 4.35; N, 5.99; S, 13.50

3,6-Di-(3'-ethylthio-4'-methoxycarbonylsuccinimidyl)chromen-2-one (8)

The reaction of 54 mg (0.12 mmol) of compound 5 in 3 mL dry DMSO with 27 µL ethanethiol (0.36 mmol) was carried out according to the same protocol used to obtain compound 7, giving compound 8 in 83% yield (58 mg, 0.1 mmol). FTIR (KBr) (cm$^{-1}$): 3000, 1727, 1622, 600. $^1$H-NMR (DMSO-d$_6$): δ (ppm) 8.24 (s, 1H), 7.53 (d, J=2.63, 1H), 7.36 (dd, J=9.24

Hz, J=2.67 Hz, 1H), 7.24 (d, J=9.24 Hz, 1H), 4.38 (d, 1H), 4.32 (s, 1H), 4.00 (s, 3H), 3.98 (d, J=5.6 Hz, 3H), 3.92 (d, J=5.4 Hz, 1H), 3.87 (d, J=5.6 Hz, 1H), 2.80 (m, 4H), 1.30 (t, J=7.24 Hz, 6H). $^{13}$C-NMR (DMSO-d$_6$): δ (ppm) 175.06, 172.67, 168.06, 158.44, 150.63, 137.28, 128.83, 128.32, 124.22, 119.69, 118.47, 117.21, 50.01, 46.23, 42.16, 39.12, 14.24, 12.02. HRMS expected for $C_{25}H_{24}N_2O_{10}S_2$: 576.087238; found: 576.087413.

3,6-Di-(3'-ethylthio-4'-methylsuccinimidyl)chromen-2-one (9)

The reaction of 44 mg (0.12 mmol) of compound 6 in 3 mL dry DMSO with 27 μL ethanethiol (0.36 mmol) was carried out according to the same protocol used to obtain compound 7, giving compound 9 in 84% yield (49 mg, 0.1 mmol). FTIR (KBr) (cm$^{-1}$): 1720, 1620, 600. $^1$H-NMR (CDCl$_3$): δ (ppm) 8.21 (s, 1H), 7.57 (d, J=2.53 Hz, 1H), 7.39 (dd, J=8.47 Hz, J=2.67 Hz, 1H), 7.26 (d, J=8.35 Hz, 1H), 3.84 (s, 1H), 3.12 (s, 1H), 3.07 (s, 1H, 2.83 (m, 4H), 1.93 (d, J=7.08 Hz, 3H), 1.90 (d, J=7.25 Hz, 3H), 1.30 (t, J=7.28 Hz, 6H). $^{13}$C-NMR (DMSO-d$_6$): δ (ppm) 175.04, 172.32, 167.92, 156.34, 150.73, 137.21, 129.87, 128.65, 124.34, 118.03, 117.04, 38.53, 34.29, 26.02, 20.68, 14.27, 11.67. HRMS expected for $C_{23}H_{24}N_2O_6S_2$: 488.107580; found: 488.107213.

3,6-(4,4'-bis(methylmercapto-3-succinimidyl)benzophenone)chromen-2-one (10)

Compound 4 (42 mg, 0.13 mmol) and BMMB (34 mg, 0.13 mmol) were placed in a 10-mL round bottom flask. Chloroform (2.5 mL) was then added with stirring. To this suspension triethylamine (52 μL, 0.39 mmol) was then added and the reaction mixture was heated to reflux for 12 h. The mixture was cooled to room temperature. A 50-mL aliquot of water was then added and the solution was extracted 4 times with 20 mL dichloromethane. The organic layers were combined, dried over MgSO$_4$ and removed under reduced pressure. The resulting product was then purified by flash chromatography (20:80 EtOAc:hexane). Compound 10 was thus obtained as a beige solid in 78% yield (61 mg, 0.10 mmol). mp:>220° C. (dec). FTIR (KBr) (cm$^{-1}$): 1720, 1654, 1605, 602. $^1$H-NMR (CDCl$_3$): δ (ppm) 7.81 (d, J=8.0 Hz, 4H), 7.73 (d, J=7.9 Hz, 4H), 7.60 (d, J=9.4 Hz, 1H), 7.52 (s, 1H), 7.45 (d, J=9.6 Hz, 1H), 7.39 (s, 1H), 4.40 (d, J=5.6 Hz, 1H), 3.96 (d, J=5.5 Hz, 1H), 3.68 (s, 4H), 3.26 (q, J=8.8 Hz, 2H), 2.65 (d, J=5.6 Hz, 2H). $^{13}$C-NMR (CDCl$_3$): δ (ppm) 195.92, 176.77, 175.24, 159.32, 148.90, 147.76, 143.07, 136.90, 136.51, 130.96, 130.25, 129.88, 129.38, 127.62, 127.08, 121.77, 117.69, 105.43, 36.70, 35.34, 28.47. HRMS expected for $C_{32}H_{22}N_2O_7S_2$: 611.09250; found: 611.09267.

6-Nitro-3-p-nitrophenylchromen-2-one (11)

2-Hydroxy-5-nitrobenzaldehyde (250 mg, 1.50 mmol) and p-nitrophenylacetic acid (271 mg, 1.50 mmol) were placed in a dry 25-mL round bottom flask. Acetic anhydride (2.8 mL, 30 mmol) was then added with stirring. To this suspension sodium hydride (60 mg, 1.50 mmol) was then added in small aliquots (60% oil suspension) and the reaction mixture was heated to 100° C. for 3 h. Then, 100 μL of water and 3 mL of acetic acid were added. The mixture was cooled to 4° C. for one hour and then filtered. The solid was rinsed with cold glacial acetic acid and placed in a 100-mL flask, to which was added 30 mL of toluene, which was then removed by rotary evaporation. This addition and removal of toluene was repeated two more times to remove the last traces of acetic acid. The resulting solid was then dried under vacuum to give a beige powder (11) in 70% yield (325 mg, 1.05 mmol). mp: 250° C. (dec). FTIR (KBr) (cm$^{-1}$): 1620, 1480, 1750, 1540, 1350. $^1$H-NMR (DMSO-d$_6$): δ (ppm) 8.80 (d, J=2.6 Hz, 1H), 8.62 (s, 1H), 8.47 (dd, J=9.1 Hz, J=2.7 Hz, 1H), 8.37 (dd, J=8.9 Hz, J=2.0 Hz, 1H), 8.02 (dd, J=8.9 Hz, J=2.0 Hz, 2H), 7.71 (d, J=9.1 Hz, 1H). $^{13}$C-NMR (DMSO-d$_6$): δ (ppm) 159.43, 157.87, 148.46, 144.68, 142.30, 141.50, 130.85, 127.92, 125.77, 124.51, 120.53, 118.64. HRMS: expected, 312.038236; found, 312.039100. Elemental analysis for $C_{15}H_8N_2O_6$: expected: C, 57.70; H, 2.58; N, 8.97; found: C, 57.37; H, 2.62; N, 8.78.

6-Amino-3-p-aminophenylchromen-2-one (12)

Following the same protocol used to obtain diamine 2, palladium on carbon (10% water) (0.322 g, 1/10$^{th}$ of the mass of 11) and a solution of sodium borohydride (1.21 g, 32.9 mmol) in water (22.6 mL) were used to reduce a suspension of compound 11 (4.03 g, 12.9 mmol) in methanol (775 mL). In this way, compound 12 (2.04 g, 8.1 mmol) was obtained as a yellow solid in 63% yield. FTIR (KBr) (cm$^{-1}$): 3180, 3120, 1700, 1610, 850. $^1$H-NMR (DMSO-d$_6$): δ (ppm) 7.84 (s, 1H), 7.46 (d, J=8.5 Hz, 2H), 7.08 (d, J=8.6 Hz, 1H), 6.79 (d, J=8.5 Hz, 1H), 6.77 (s, 1H), 6.60 (d, J=7.8 Hz, 2H), 5.32 (ds, 3H), 5.15 (ds, 3H). $^{13}$C-NMR (DMSO-d$_6$): δ (ppm) 163.34, 150.20, 146.43, 145.43, 137.99, 130.38, 127.88, 123.18, 11.33, 118.85, 116.94, 114.39, 111.04. HRMS: expected, 252.089878; found, 252.089846. Elemental analysis for $C_{15}H_{12}N_2O_2$: expected: C, 71.42; H, 4.79; N, 11.10; found: C, 71.30; H, 4.58; N, 10.92

6-Maleimidyl-3-p-maleimidylphenylchromen-2-one (13)

The protocol used to obtain compound 4 was followed, using diamine 12 (400 mg, 1.59 mmol) and maleic anhydride (777 mg, 4.77 mmol) in 15 mL chloroform and then 15 mL acetic anhydride (0.1, mol) and 130 mg sodium acetate (1.59 mmol). In this way, 13 was obtained as a beige solid and dried over vacuum to give 13 in 20% yield (131 mg, 0.32 mmol). mp: >250° C. (dec). FTIR(KBr) (cm$^{-1}$): 2923, 1721, 1615, 1520, 1347, 853. $^1$H-NMR (DMSO-d$_6$): δ (ppm) 8.36 (s, 1H), 7.87 (dd, J=8.9 Hz, J=2.0 Hz, 2H), 7.85 (d, J=8.6 Hz, 1H), 7.60 (dd, J=8.6 Hz, J=2.6 Hz, 1H), 7.59 (d, J=2.6 Hz, 1H), 7.45 (dd, J=8.9 Hz, J=2.0 Hz, 2H), 7.24 (d, 4H). $^{13}$C-NMR (DMSO-d$_6$): δ (ppm) 169.94, 159.60, 152.04, 141.00, 134.90, 133.82, 131.96, 130.50, 130.11, 129.25, 127.88, 126.95, 126.50, 119.77, 117.40, 104.30. HRMS: expected, 412.069536; found, 412.069540. Elemental analysis for $C_{23}H_{12}N_2O_6$: expected: C, 66.99; H, 2.93; N, 6.79; found: C, 66.13; H, 2.84; N, 6.64.

6-(3'-Ethylthiosuccinimidyl)-3-p-(3'-ethylthiosuccinimidyl)phenylchromen-2-one (14)

To a solution of compound 13 (20 mg, 0.049 mmol) in 2.5 mL of dry DMSO was added 110 μL of ethanethiol (0.147 mmol) and the solution was allowed to stir overnight at room temperature. A 100-mL aliquot of water was then added and the solution was extracted 4 times with 20 mL dichloromethane. The organic layers were combined, dried over MgSO$_4$ and removed under reduced pressure, apart from traces of residual DMSO, giving compound 14 in 89% yield (22 mg, 0.044 mmol). FTIR (KBr) (cm$^{-1}$): 2950, 1713, 1602, 835, 756. $^1$H-NMR (DMSO-d$_6$): δ (ppm) 8.39 (s, 1H), 7.86 (d, J=8.5 Hz, 2H), 7.74 (d, J=2.5 Hz, 1H), 7.60 (d, J=9.1 Hz, 1H), 7.55 (dd, J=8.9 Hz, J=2.5 Hz, 1H), 7.38 (d, J=8.6 Hz, 2H), 4.17 (m, 2H), 3.42 (dd, J=8.2 Hz, J=2.0 Hz, 1H), 3.38 (dd, J=8.2 Hz, J=2.0 Hz, 1H), 2.84 (m, 4H), 2.76 (d, J=5.6 Hz, 1H), 2.71 (d, J=5.5 Hz, 1H), 1.25 (t, J=7.3 Hz, 6H). $^{13}$C-NMR (DMSO-d$_6$): δ (ppm) 176.96, 175.33, 160.45, 153.44, 141.38, 135.52, 133.56, 131.38, 130.26, 129.42, 127.89, 127.79, 120.76, 117.79, 37.26, 25.82, 20.49, 19.31, 15.31. HRMS expected for $C_{27}H_{24}O_6S_2$: 537.11680; found: 537.11642.

1,5-Dimaleimidylnaphthalene (15)

The protocol used to obtain compound 4 was followed, using a suspension of 300 mg of 1,5-diaminonaphtalene (1.90 mmol) in 20 mL of dry chloroform, 560 mg (5.70 mmol) maleic anhydride, and then 15 mL acetic anhydride and 59 mg (0.70 mmol) of sodium acetate. Compound 15 was thus obtained as a yellow solid in 71% yield (428 mg, 1.35 mmol). mp>230° C. (dec). FTIR (KBr) (cm$^{-1}$): 3070, 1705. $^1$H-NMR (DMSO-d$_6$): δ (ppm) 7.87 (d, J=7.80 Hz, 1H), 7.70 (t, J=8.49 Hz, 1H), 7.62 (d, J=7.38 Hz, 1H), 7.32 (s, 4H). $^{13}$C-NMR (DMSO-d$_6$): δ (ppm) 170.03, 134.61, 130.70, 128.24, 127.62, 126.31, 123.83. HRMS expected: 318.064056; found: 318.064142. Elemental analysis for $C_{18}H_{10}N_2O_4$ expected: C, 67.93; H, 3.17; N, 8.80; found: C, 67.05; H, 3.13; N, 8.62.

1,5-Di(3'-ethylthiosuccinimidyl)naphthalene (16)

The same protocol used to obtain 14 was followed, using 38 mg of compound 15 (0.12 mmol) in 3 mL anhydrous DMSO (3 mL) with 27 μL of ethanethiol (0.36 mmol) to give compound 16 in 87% yield (46 mg, 0.10 mmol). FTIR (KBr) (cm$^{-1}$): 3000, 1620, 600. $^1$H-NMR (DMSO-d$_6$): δ (ppm) 8.00 (d, J=8.16 Hz, 1H), 7.78 (t, J=7.82 Hz, 1H), 7.75 (m, 2H), 7.57 (d, J=8.04 Hz, 1H), 7.51 (d, J=8.02 Hz, 2H), 4.42 (d, J=5.20 Hz, 1H), 4.22 (d, J=5.00 Hz, 1H), 3.64 (m, 1H), 3.42 (m, 1H), 3.34 (m, 6H), 1.89 (t, 6H). $^{13}$C-NMR (DMSO-d$_6$): δ (ppm) 175.95, 174.40, 162.92, 129.81, 129.56, 128.99, 128.84, 128.35, 127.06, 126.63, 126.31, 125.82, 124.01, 122.48, 36.43, 35.91, 24.70, 24.40, 13.86. HRMS expected for $C_{22}H_{22}N_2O_4S_2$: 442.102100; found: 442.102312.

3,6-Dinitro-1,8-naphthalic anhydride (17)

Sulfuric acid (40.0 mL, 0.75 mol) was placed in a 100-mL flask to which was added 1,8-naphtalic anhydride (10.0 g, 50.5 mmol). The solution was cooled to 5° C. in an ice bath. Nitric acid (10 mL, 0.22 mol) was added drop by drop, taking care to not allow the temperature to exceed 20° C. The solution was then heated to 60° C. for 90 min and then cooled again to 4° C. for 24 h to induce precipitation. The resulting precipitate was removed by filtration and washed with cold glacial acetic acid. The solid was then washed with toluene (3×50 mL) that was subsequently removed by rotary evaporation, repeating this process two more times to remove trace acetic acid, giving 17 as a beige powder (10.31 g, 37.8 mmol) in 72% yield. mp 208-210° C. (lit 208° C. FTIR (KBr) (cm$^{-1}$): 3098, 2897, 1707, 1617, 1552, 1336, 1260. $^1$H-NMR (acetone-d$_6$): δ (ppm) 9.80 (d, J=2.23 Hz, 2H), 9.05 (d, J=2.13 Hz, 2H). $^{13}$C-NMR (DMSO-d$_6$): δ (ppm) 159.75, 148.14, 134.62, 133.28, 131.62, 128.06, 123.07. HRMS expected: 288.00185; found: 288.00144.

N-(3,6-Dinitro-1,8-naphthalyl)-L-aspartic acid dimethyl ester (18)

Compound 17 (300 mg, 1.06 mmol) and L-aspartic acid dimethyl ester hydrochloride (217 mg, 1.06 mmol) were added to a 25-mL flask containing 10 mL of dry acetonitrile. Triethylamine (180 μL, 1.27 mmol) was added drop by drop to give a violet solution that was heated to 90° C. for 60 h. After cooling the solution to room temperature, the solvent was removed through rotary evaporation and the solid obtained was purified by flash chromatography (70:30 hexane:EtOAc). The solvent was evaporated to give compound 18 as a beige powder (229 mg, 0.53 mmol) in 50% yield. mp: 128-129° C. FTIR (KBr) (cm$^{-1}$): 3083, 2954, 1740, 1678, 1536, 1319, 748. $^1$H-NMR (CDCl$_3$): δ (ppm) 9.44 (d, J=2.08 Hz, 2H), 9.39 (d, J=2.07 Hz, 2H), 6.17 (dd, J=7.88 Hz, J=6.29 Hz, 1H), 3.72 (s, 3H), 3.63 (s, 3H), 3.44 (dd, J=16.84 Hz, J=6.26 Hz, 1H), 3.01 (dd, J=16.84, J=7.94 Hz, 1H). $^{13}$C-NMR (CDCl$_3$): δ (ppm) 170.53, 168.37, 160.99, 147.46, 131.97, 130.90, 130.80, 127.58, 124.54, 52.98, 52.00, 50.12, 33.35. HRMS expected for $C_{18}H_{14}N_3O_{10}$: 432.067919; found: 432.068765. $α_D$=−33° (c=1, CHCl$_3$)

N-(3,6-Diamino-1,8-naphthalyl)-L-aspartic acid dimethyl ester (19)

Compound 18 (220 mg, 0.51 mmol) was placed in a 50-mL flask and 20 mL of THF and palladium on carbon (10% wet) (22 mg, 1/10$^{th}$ the mass of 18) were added. The reaction mixture was then placed in a hydrogenation reactor and left under 150 psi pressure for 24 h. The mixture was then filtered through Celite and the filtrate was evaporated under reduced pressure. The residue was purified by flash chromatography (70:30 EtOAc:CHCl$_3$). The solvent was then removed by rotary evaporation to give compound 19 (92.5 mg, 0.25 mmol) as an orange powder in 49% yield. mp: 175-177° C. FTIR (KBr) (cm$^{-1}$): 3380, 1748, 1625, 1316, 797. $^1$H-NMR (DMSO-d$_6$): δ (ppm) 7.59 (d, J=1.90 Hz, 2H), 6.97 (d, J=1.90 Hz, 2H), 6.02 (dd, J=8.00 Hz, J=5.43 Hz, 1H), 5.74 (s, 4H), 3.61 (s, 6H), 3.28 (dd, J=16.49 Hz, J=8.59 Hz, 1H), 2.85 (dd, J=16.53 Hz, J=5.00 Hz, 1H). $^{13}$C-NMR (DMSO-d$_6$): δ (ppm) 171.81, 170.66, 164.56, 148.76, 136.60, 122.74, 118.43, 115.51, 111.18, 111.11, 53.50, 50.73, 49.52, 34.76. HRMS expected for $C_{18}H_{17}N_3O_6$: 371.111736; found: 371.113454. $α_D$=−150° (c=0.1, DMSO)

N-(3,6-Dimaleimidyl-1,8-naphthalyl)-L-aspartic acid dimethyl ester (20)

Compound 19 (200 mg, 0.54 mmol) and maleic anyhdride (159 mg, 1.62 mmol) were placed in a dry 50-mL round-bottom flask. Chloroform (15 mL) was added and the solution was heated to reflux for 24 h. The solution was then cooled to room temperature and filtered. The brown precipitate thus recovered was dried under reduced pressure. The solid was then placed in a 25-mL round-bottom flask to which sodium acetate (21 mg, 0.37 eq) and acetic anhydride (10 mL) were added. The solution was heated to 100° C. for 90 min. The solvent was then removed through evaporation and the resulting solid was dissolved in ethyl acetate. The solution was cooled to 4° C. for 48 h and the recovered precipitate was washed with 25 mL of 80:20 water-DMSO and then 25 mL of water. The solid was then dissolved in a minimal volume of hot ethyl acetate and hexane was added to induce precipitation of the expected product (20) (53 mg, 0.10 mmol) as an orange powder in 19% yield. mp>20° C. (dec). FTIR (KBr) (cm$^{-1}$): 3102, 1717, 1669, 1413. $^1$H-NMR (DMSO-d$_6$): δ (ppm) 8.60 (d, J=1.83 Hz, 2H), 8.58 (d, J=1.86 Hz, 2H), 7.32 (s, 4H), 6.12 (dd, J=7.96 Hz, J=5.38 Hz, 1H), 3.64 (s, 3H), 3.63 (s, 3H), 3.32 (dd, J=16.52 Hz, J=8.60 Hz, 1H), 2.97 (dd, J=16.53 Hz, J=5.03 Hz, 1H). $^{13}$C-NMR (DMSO-d$_6$): δ (ppm) 171.77, 170.63, 170.33, 163.45, 136.08, 132.70, 132.35, 132.16, 130.80, 125.85, 123.47, 53.72, 52.83, 50.16, 34.46. HRMS expected: 532.099219; found: 532.098040. $α_D$=−85° (c=0.1, DMSO)

N-(3,6-Di(3'-ethylthiosuccinimidyl)-1,8-naphthalyl)-L-aspartic acid dimethyl ester (21)

The reaction of 26 mg (0.49 mmol) of compound 20 in 2.5 mL dry DMSO with 110 μL ethanethiol (0.147 mmol) was carried out according to the same protocol used to obtain compound 7, giving compound 21 in 89% yield (29 mg, 0.044 mmol). FTIR (KBr) (cm$^{-1}$): 3104, 1715, 1671, 1528, 756. $^1$H-NMR (DMSO-d$_6$): δ (ppm) 8.59 (d, J=1.82 Hz, 2H), 8.52 (d, J=1.78 Hz, 2H), 6.08 (dd, J=7.86, J=5.29 Hz, 1H), 4.20 (q, J=8.66 Hz, 2H), 3.61 (m, 10H), 3.41 (dd, J=16.46, J=8.56 Hz, 1H), 2.88 (m, 5H), 1.25 (t, J=8.27 Hz, 6H). $^{13}$C-NMR (DMSO-d$_6$): δ (ppm) 175.86, 173.73, 170.26, 169.15, 168.80, 161.87, 134.58, 131.96, 131.20, 130.68, 129.30, 127.72, 127.34, 126.98, 124.74, 124.46, 121.98, 121.73, 52.18, 51.32, 48.64, 32.93, 24.44, 18.98, 17.78, 13.84. HRMS expected for $C_{30}H_{29}O_{10}S_2$: 655.12943; found: 655.12902.

Capillary Electrophoresis

After reaction of 1 mM 1 with 0.25-3 mM 3-mercaptopropionic acid in DMSO-H$_2$O 1.9 overnight, the fluorescence of the reaction mixture was measured. To this mixture was then added 3 equivalents of ethanethiol, converting all unreacted and monothiolated adducts to dithiolated adducts. Subsequent separation by CE permitted the distinction between the monocarboxylated dithiol adducts and the dicarboxylated dithiol adducts produced during the reaction in DMSO. Injection of ~20 nL of the reaction mixture diluted in 0.1 M CHES buffer at pH 9.0 and application of 15 kV potential led to the elution of the monothiolated adduct at 4.42 minutes and the dithiolated adduct at 8.88 minutes. Their relative concentrations were calculated by the areas under their peaks, recorded UV detection at 370 nm. Note that the prior conversion to dithiol adducts was necessary since the maleimide group reacts slowly to form side-products in the pH 9 buffer used for CE analysis.

REFERENCES

1. Liang, F.; Holt, I.; Pertea, G.; Karamycheva, S.; Salzberg, S.; Quackenbush, J.: "Gene index analysis of the human genome estimates approximately 120,000" Nat. Genet. 2000, 25, 239-240.

2. Roest Crollius, H.; Jaillon, O.; Dasilva, C.; Bouneau, L.; Fischer, C.; Fizames, C.; Wincker, P.; Brottier, P.; Quetier, F.; Saurin, W.; Weissenbach, J.: "Estimate of human gene number provided by genome-wide analysis using", Nat. Genet. 2000, 25, 235-238.

3. Ewing, B.; Green, P.: "Analysis of expressed sequence tags indicates 35,000 human genes", Nat. Genet. 2000, 25, 232-234.

4. For example, see Haughland, R. P. In Handbook of Fluorescent Probes and Research Chemicals, Molecular Probes, Eugene, Oreg., 1992, 5th Edn.

5. Sipple, T. O.: "New fluorochromes for thiols: maleimide and iodoacetamide derivatives of 3-phenyl coumarin fluorophore", J. Histochem. Cytochem. 1981, 29, 314-321.

6. Corrie, J. E. T.: "Thiol-reactive Fluorescent Probes for Protein Labelling", J. Chem. Soc. Perkin Trans. 1 1994, 2975-2982.

7. For a recent review, see: Zhang, J.; Campbell, R. E.; Ting, A. Y.; Tsien, R. Y.: "Creating New Fluorescent Probes for Cell Biology", Nature Rev. 2002, 3, 906-918.

8. Tsien, R. Y.: "The Green Fluorescent Protein", Annu. Rev. Biochem. 1998, 67, 509-544.

9. Griffin, B. A.; Adams, R. S.; Tsien, R. Y.: "Specific Covalent Labeling of Recombinant Protein Molecules Inside Live Cells", Science 1998, 281, 269-272.

10. Griffin, B. A.; Adams, S. R.; Jones, J.; Tsien, R. Y.: "Fluorescent labeling of recombinant proteins in living cells with FlAsH", Methods Enzymol. 2000, 327, 565-578.

11. Gaietta, G.; Deerinck, T. J.; Adams, S. R.; Bouwer, J.; Tour, O.; Laird, D. W.; Sosinsky, G. E.; Tsien, R. Y.; Ellisman, M. H.: "Multicolor and Electron Microscopic Imaging of Connexin Trafficking", Science 2002, 296, 503-507.

12. Adams, S. R.; Campbell, R. E.; Gross, L. A.; Martin, B. R.; Walkup, G. K.; Yao, Y.; Llopis, J.; Tsien, R. Y.: "New Biarsenical Ligands and Tetracysteine Motifs for Protein Labeling In Vitro and In Vivo: Synthesis and Biological Applications", J. Am. Chem. Soc. 2002, 124, 6063-6076.

13. Girouard, S.; Keillor, J. W. "Élaboration d'un fluorophore permettant une étude d'apposition protéique", M. Sc. Thesis, Université de Montréal, 2000.

14. Houle, M.-H.; Keillor, J. W. "Synthèse d'un composé fluorogénique permettant l'étude de l'apposition protéique", M. Sc. Thesis, Université de Montréal, 2003.

15. Kanaoka, Y.; Sekine, T.; Machida, M.; Sôma, Y.; Tanizawa, K.; Ban, Y.: "Studies on Protein-Sulfuryl Reagent. Synthesis of Benzimidazole Derivatives of Maleimide; Fluorescent Labeling of Maleimide", Chem. Pharm. Bull. 1964, 12, 127.

16. Kuznetsova, N. A.; Kaliya, O. L.: "The photochemistry of coumarins", Russ. Chem. Rev. 1992, 61, 683.

17. Langmuir, M. E.; Yang, J. -R.; Moussa, A. M.; Laura, R.; LeCompte, K. A.: "New Naphtopyranone Based Fluorescent Thiol Probes", Tetrahedron Lett. 1995, 36, 3989.

18. Yang, J. -R.; Langmuir, M. E.: "Synthesis and Properties of a Maleimide Fluorescent Thiol Reagent Derived a Naphtopyranone", J. Heterocyclic Chem. 1991, 28, 1177.

19. Girouard, S.; Houle, M. -H.; Grandbois, A.; Keillor, J. W., Michnick, S.: "Synthesis and Characterization of Novel Fluorogens Designed for Application to Protein Labelling", manuscript in preparation.

20. Girouard, S.; Ghaddar, G.; Keillor, J. W., Michnick, S. "Design Of Fluorogens For The Selective Fluorescent Labeling Of Target Proteins In Vivo.", manuscript in preparation.

21. Abate, C.; Luk, D.; Gentz, R.; Rauscher III, F. J.; Curran, T.: "Expression and purification of the leucine zipper and DNA-binding domains of Fos and Jun: Both Fos and Jun contact DNA directly", Proc. Natl. Acad. Sci. 1990, 87, 1032-1036.

22. O'Shea, E. K.; Rutkowski, R.; Kim, P. S.: "Mechanism of Specificity in the Fos-Jun Oncoprotein Heterodimer", Cell 1992, 68, 699-708.

23. Furthermore, this plasmid was made available through the generous donation of Dr. T. Curran of St. Jude Children's Research Hospital, corresponding author of reference 21.

24. Russ, A.; Bump, E. A.: "Detection and quantitation of biological sulfhydryls", Methods Biochem. Anal. 1988, 33, 165-241.

25. Kokotos, G.; Tzougrakic, C. "Synthesis and Study of Substituted Coumarins. A Facile Preparation of D,L-o-Tyrosine", J. Heterocyclic Chem. 1986, 23, 87.

26. Trivedi, K.; Sethna, S. "3-Hydroxycoumarins", J. Org. Chem. 1960, 25, 1817.

27. Reddy P. Y.; Kondo S.; Fujita S.; Toru T. "Efficient Synthesis of Fluorophore-Linked Maleimide Derivatives", Synthesis 1998, 999.

28. Braña, M. F.; Castellano, J. M.; Morán, M.; Pérez de Vega, M. J.; Romerdahl, C. R.; Qian, X. -D.; Bousquet, P.; Emiling, F.; Schlick, E.; Keilhauer, G. "Bis-naphthalimide: a new class of antitumoragents", Anti-cancer Drug Design 1993, 8, 257-268.

29. Blažević, N.; Kolbah, D.; Belin, B.; Šunjić, V.; Kajfež, F. "Hexamethylenetetramine, A Versatile Reagent in organic Synthesis", Synthesis 1979, 161-176.

30. Golden J. H. "Poly-p-xylylene and Related Polymers", J. Chem. Soc. 1961, 1604.

31. Evans, B. S.; Abdelkader, M.; Buyle Padia, A.; Hall, H. K. "Synthesis and Reactions of a-Carbomethoxy-N-phenylmaleimide and Related Electrophilic Ethylenes", J. Org. Chem. 1989, 54, 2848.

32. Lakowiez J. R., "Principles of Fluorescence Spectroscopy" Kluwer Academic/Plenum Publishers, 2nd edition (1999).

33. Kayser, M. M.; Breau, L.; Eliev, S.; Morand P.; Ip, H. S. "Regioselectivity control in metal hydride reduction of substituted maleic anhydrides", Can. J. Chem. 1986, 64, 104.

34. Burdette, S. C.; Walkup, G. K.; Spingler, B.; Tsien R. Y.; Lippard S. J. "Fluorescent Sensors for Zn2+ Based on a Fluorescein Platform: Synthesis, Properties and Intracellular Distribution", J. Am. Chem. Soc. 2001, 123, 7831-7841.

35. To accommodate the change of expression vector from pDS56 (see reference 21) to pQE32, primers were used to shift the open reading frame (5'-CACACAGGATCCACG-GTCGTGCGCA-3') and remove a Pst I restriction site (CT-GCA/G) through a silent mutation (CAGàGAG) and to mutate Leu56 to Cys (5'-GGTTTCCGCCTGGAGGGT-GTCGGTACATTCACGACGGCA-GT-3').

36. According to molecular modeling based on co-ordinates from Protein DataBank file 1FOS.

37. Flint, D. G.; Kumita, J. R.; Smart, O. S.; Woolley, G. A.: "Using an Azobenzene Cross-Linker to Either Increase or Decrease Peptide Helix Content upon Trans-to-Cis Photoisomerisation", Chem. & Biol. 2002, 9, 391-397.

38. Marqusee, S.; Robbins, V. H.; Baldwin, R. L.: "Unusually stable helix formation in short alanine-based peptides", Proc. Natl. Acad. Sci. USA 1989, 86, 5286-5290.

39. Merutka, G.; Stellwagen, E.: "Positional Independence and Additivity of Amino Acid Replacements on Helix Stability in Monomeric Peptides", Biochemistry 1990, 29, 894-898.

40. Penel, S.; Morrison, R. G.; Mortishire-Smith, R. J.; Doig, A. J.: "Periodicity in a-Helix Lengths and C-Capping Preferences", J. Mol. Biol. 1999, 293, 1211-1219.

41. Muñoz, V.; Serrano, L.: "Development of the Multiple Sequence Approximation Within the AGADIR Model of a-Helix Formation: Comparison with Zimm-Bragg and Lifson-Roig Formalisms", Biopolymers 1997, 41, 495-509.

42. The AGADIR algorithm is available on-line at http://www.embl-heidelberg.de/Services/serrano/agadir/agadir-start.html.

43. Remy, I and S. W. Michnick, A cDNA library functional screening strategy based on fluorescent protein complementation assays to identify novel components of signaling pathways. Methods 2004, 32, 381-388.

44. Hancock, J. J.: "Ras proteins: different signals from different locations", Nat. Rev. Mol. Cell. Biol. 2003, 4, 373-385.

45. Campbell, S. L.; Khosravi-Far, R.; Rossman, K. L.; Clark, G. J.; Der, C. J.: "Increasing complexity of Ras signaling", Oncogene 1998, 17, 1395-1413.

46. Chiu, V. K.; Biovna, T.; Hach, A.; Sajous, J. B.; Silletti, J.; Wiener, H.; Johnson, R. L.; Cox, A. D.; Philips, M. R.: "Ras signalling on the endoplasmic reticulum and the Golgi", Nature Cell Biol. 2002, 4, 343-350.

47. Jares-Edjman, E. A., Jovin, T. M.: "FRET Imaging", Nature Biotech. 2003, 21, 1387-1395.

48. Schebner, K. A.; Zhang, Z.; Cole, P. A.: "Merging fluorescence resonance energy transfer and expressed protein ligation to analyze protein-protein interactions", Anal. Biochem. 2003, 317, 226-232.

49. Choi, J; Chen, J; Schreiber, S. L.; Clardy, J.: "Structure of the FKBP12-Rapamycin Complex Interacting with Binding Domain of Human FRAP", Science 1996; 273, 239-242.

50. Nassar, N.; Horn, G.; Herrmann, C.; Scherer, A.; McCormick, F.; Wittinghofer, A.: "The 2.2 Å crystal structure of the Ras-binding domain of the serine/threonine kinase c-Raf1 in complex with Rap1A and a GTP analogue", Nature 1995, 375, 554-560.

51. Remy, I.; Michnick, S. W.: "Clonal selection and in vivo quantitation of protein interactions with protein-fragment complementation assays", Proc. Natl. Acad. Sci. USA 1999, 96, 5392-5399.

What is claimed is:

1. An assay method for detecting target proteins having sterically unhindered sulfhydryl groups, said assay comprising:

generating:

1) at least a first dimaleimide molecule, said dimaleimide molecule having the following formula:

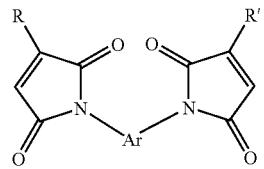

wherein each R or R', independently, is $R_a$ or $OR_a$ and $R_a$ is H, $C_1$-$C_4$ alkyl, $CH_2CO_2H$, $CH_2CH_2OH$ or CN and Ar is a rigid aromatic skeleton and selected from the group consisting of fluorescein, rhodamine, eosin, thionine, safranin, fluorescent compounds having naphthyl groups and coumarin; wherein the substituent maleimide groups are positioned around the aromatic core in such a manner that they are separated by 5, 10 or 15 Å, conferring complementarity for reaction of both maleimide groups of the fluorogen with the sulthydryl groups of said target protein having sterically unhindered sulfhydryl groups; or said dimaleimide molecule has the following formula:

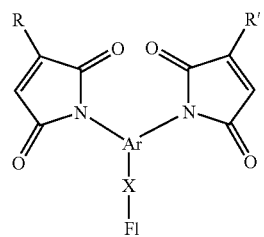

wherein each R or R', independently, is $R_a$ or $OR_a$ and $R_a$ is H, $C_1$-$C_4$ alkyl, $CH_2CO_2H$, $CH_2CH_2OH$ or CN and Ar is a rigid aromatic skeleton comprising one aromatic ring or two to four fused aromatic rings selected from the group consisting of phenyl, naphthyl, anthracene, fluorene, pyridine, pyrimidine, purine, and indole, X is a spacer sequence that includes $C_1$-$C_4$ alkyl, $OCH_2CH_2O$, $NHCO(C_1$-$C_4CH_2$ alkyl)NHCO, CONH($C_1$-$C_4CH_2$ alkyl)NHCO, NHCO($C_1$-$C_4CH_2$ alkyl)CONH, CONH($C_1$-$C_4CH_2$ alkyl)CONH, and Fl is a fluorophore selected from the group consisting of fluorescein, rhodamine, eosin, thionine, safranin, and coumarin; wherein the substituent maleimide groups are also positioned around the aromatic core in such a manner that they are separated by 5, 10 or 15 Å, conferring complementarity for reaction of both maleimide groups of the fluorogen with the sulfhydryl groups of said target protein having sterically unhindered sulfhydryl groups 2) at least a target protein having sterically unhindered sulfhydryl groups, or a target protein linked or fused to a protein of interest; or 3) nucleic acid molecules that code for said target protein or a target protein fused to a protein of interest as defined in 2) and subsequently allowing said nucleic acid molecules to produce their coded products; then,
(A) allowing reaction of said target protein having sterically unhindered sulfhydryl groups or a target protein fused to a protein of interest with said dimaleimide molecule; and
(B) detecting a a fluorescent signal from said complex of target protein or a target protein fused to a protein of interest and dimaleimide molecule.

2. An assay method for detecting biomolecular interactions between a first interacting protein and a second interacting protein, wherein said first interacting protein is linked or fused to a first target protein having sterically unhindered sulfhydryl groups, and said second interacting protein is linked or fused to a second target protein having sterically unhindered sulfhydryl groups, said method comprising:
generating:
1) at least a first dimaleimide molecule said dimaleimide molecule having the following formula:

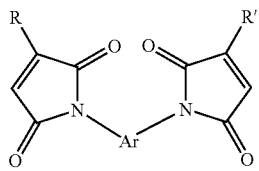

wherein: each R or R', independently, is $R_a$ or $OR_a$ and $R_a$ is H, $C_1$-$C_4$ alkyl, $CH_2CO_2H$, $CH_2CH_2OH$ or CN and Ar is a rigid aromatic skeleton selected from the group consisting of fluorescein, rhodamine, eosin, thionine, safranin, fluorescent derivatives having naphthyl groups and coumarin; wherein the substituent maleimide groups are positioned around the aromatic core in such manner that they are separated by 5, 10 or 15 Å, conferring complementarity for reaction of both maleiniide groups of the flourgen with the sulfhydryl groups of said target proteins having sterically unhindered sulfhydryl groups; or said dimaleimide molecule has the following formula:

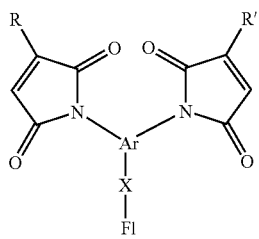

wherein each R or R', independently, is $R_a$ or $OR_a$ and $R_a$ is H, $C_1$-$C_4$ alkyl, $CH_2CO_2H$, $CH_2CH_2OH$ or CN and Ar is a rigid aromatic skeleton comprising one aromatic ring or two to four fused aromatic rings selected from the group consisting of phenyl, naphthyl, anthracene, fluorene, pyridine, pyrimidine, purine, and indole, X is a spacer sequence selected from the group consisting of $C_1$-$C_4$ alkyl, $OCH_2CH_2O$, $NHCO(C_1$-$C_4CH_2$ alkyl)NHCO, $CONH(C_1$-$C_4CH_2$ alkyl)NHCO, $NHCO(C_1$-$C_4CH_2$ alkyl)CONH, $CONH(C_1$-$C_4CH_2$ alkyl)CONH, and Fl is a fluorophore selected from the group consisting of fluorescein, rhodamine, eosin, thionine, safranin, and coumarin; wherein the substituent maleimide groups are also positioned around the aromatic core in such a manner that they are separated by 5, 10 or 15 Å, conferring complementarity for reaction of both maleimide groups of the fluorogen with the sulfhydryl groups of said target proteins having sterically unhindered sulfhydryl groups; and 2) at least a first target protein having sterically unhindered sulfhydryl groups linked or fused to first interacting protein, or
3) nucleic acid molecules that code for said first target protein or a first target protein fused to said first interacting protein as defined in 2) and subsequently allowing said
nucleic acid molecules to produce their coded products and then,
(A) allowing reaction of said first target protein having sterically unhindered sulfhydryl groups linked or fused to said first interacting protein with said dimaleimide molecule; and then
(B) generating
4) at least a second dimaleimide molecule as defined in step 1; and
5) at least a second target protein having sterically unhindered sulfhydryl groups linked or fused to a second interacting protein, or
6) nucleic acid molecules that code for said second target protein or a second target protein fused to said second interacting protein as defined in 5) and subsequently allowing said nucleic acid molecules to produce their coded products; then,
(C) allowing association of said first and second dimaleimide molecules through the interaction of said first and second target proteins having sterically unhindered sulfhydryl groups linked or fused to said first and second interacting proteins to form a complex; and
(D) detecting a fluorescent signal from said complex of target proteins having sterically unhindered sulfhydryl groups, interacting proteins and dimaleimide molecules.

3. An assay according to claim 1 or 2 where said fluorescent aromatic derivatives have overlapping excitation and emission spectra.

4. An assay according to claim 2 where proximity of said fluorophores is detected by fluorescence resonance energy transfer.

5. The method of claims 1 or 2 wherein said first dimaleimide has the following formula:

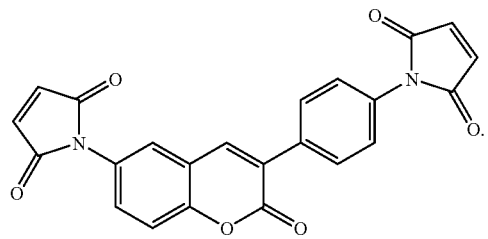

* * * * *